(12) United States Patent
Argentine et al.

(10) Patent No.: US 10,973,640 B2
(45) Date of Patent: *Apr. 13, 2021

(54) VENOUS VALVE PROSTHESES

(71) Applicant: Medtronic Vascular, Inc., Santa Rosa, CA (US)

(72) Inventors: Jeffery Argentine, Petaluma, CA (US); Todd Malsbary, Windsor, CA (US); Keith Perkins, Santa Rosa, CA (US); Travis Rowe, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 227 days.

This patent is subject to a terminal disclaimer.

(21) Appl. No.: 16/194,961

(22) Filed: Nov. 19, 2018

(65) Prior Publication Data

US 2019/0083265 A1 Mar. 21, 2019

Related U.S. Application Data

(63) Continuation of application No. 14/958,152, filed on Dec. 3, 2015, now Pat. No. 10,143,554.

(51) Int. Cl.
*A61F 2/24* (2006.01)

(52) U.S. Cl.
CPC .......... *A61F 2/2475* (2013.01); *A61F 2/2418* (2013.01); *A61F 2/2433* (2013.01);
(Continued)

(58) Field of Classification Search
CPC ........ A61F 2/24; A61F 2/2409; A61F 2/2412; A61F 2/2418; A61F 2/2469;
(Continued)

(56) References Cited

U.S. PATENT DOCUMENTS

| 5,855,597 | A | 1/1999 | Jayaraman |
| 6,458,153 | B1 | 10/2002 | Bailey et al. |

(Continued)

FOREIGN PATENT DOCUMENTS

| EP | 1900343 | 10/2015 |
| WO | 200243620 | 6/2002 |
| WO | 2006041972 | 4/2006 |

OTHER PUBLICATIONS

First Office Action and Search Report, and machine translation thereof, from counterpart Chinese Application No. 201611100212.2, dated Dec. 4, 2019, 19 pp.
(Continued)

*Primary Examiner* — Ryan J. Severson
(74) *Attorney, Agent, or Firm* — Shumaker & Sieffert, P.A.

(57) ABSTRACT

A venous valve prosthesis includes a frame and a prosthetic valve coupled to the frame. With the venous valve prosthesis implanted in a vein, the prosthetic valve includes a closed configuration wherein an outer surface of the prosthetic valve is in contact with a wall of the vein around a circumference of the prosthetic valve to prevent blood from flowing past the prosthetic valve between the wall of the vein and the outer surface of the prosthetic valve. The prosthetic valve is configured to move to an open configuration such that at least a portion of an outer wall of the prosthetic valve partially collapses away from the wall of the vein in response to antegrade blood flow through the vein to enable blood flow between the outer surface of the prosthetic valve and the wall of the vein.

25 Claims, 16 Drawing Sheets

(52) U.S. Cl.
CPC ...... *A61F 2/2436* (2013.01); *A61F 2230/001* (2013.01); *A61F 2230/0067* (2013.01); *A61F 2230/0097* (2013.01)

(58) Field of Classification Search
CPC .............. A61F 2/2475; A61F 2002/068; A61F 2002/825; A61F 2230/001
See application file for complete search history.

(56) References Cited

U.S. PATENT DOCUMENTS

| | | | |
|---|---|---|---|
| 6,494,909 B2 | 12/2002 | Greenhalgh | |
| 6,503,272 B2 | 1/2003 | Duerig et al. | |
| 6,908,481 B2 | 6/2005 | Cribier | |
| 6,958,076 B2 | 10/2005 | Acosta et al. | |
| 7,163,556 B2 | 1/2007 | Xie et al. | |
| 7,270,675 B2 | 9/2007 | Chun et al. | |
| 7,322,932 B2 | 1/2008 | Xie et al. | |
| 7,351,256 B2 | 4/2008 | Hojeibane et al. | |
| 7,416,557 B2 | 8/2008 | Drasler et al. | |
| 7,452,371 B2 | 11/2008 | Pavcnik et al. | |
| 7,485,141 B2 | 2/2009 | Majercak et al. | |
| 7,520,894 B2 | 4/2009 | Pavcnik et al. | |
| 7,569,071 B2 | 8/2009 | Haverkost et al. | |
| 7,585,321 B2 | 9/2009 | Cribier | |
| 7,597,710 B2 | 10/2009 | Obermiller | |
| 7,628,804 B2 | 12/2009 | Flagle et al. | |
| 7,686,844 B2 | 3/2010 | Case et al. | |
| 7,758,632 B2 | 7/2010 | Hojeibane et al. | |
| 7,811,315 B2 | 10/2010 | Wittens | |
| 7,811,316 B2 * | 10/2010 | Kalmann | A61F 2/2475 623/1.24 |
| 7,846,203 B2 | 12/2010 | Cribier | |
| 7,846,204 B2 | 12/2010 | Letac et al. | |
| 7,867,274 B2 | 1/2011 | Hill et al. | |
| 7,947,074 B2 * | 5/2011 | Meretei | A61F 2/2418 623/2.14 |
| 7,951,189 B2 | 5/2011 | Haverkost et al. | |
| 8,012,198 B2 | 9/2011 | Hill et al. | |
| 8,038,710 B2 * | 10/2011 | Fearnot | A61F 2/2418 623/2.17 |
| 8,109,993 B2 * | 2/2012 | Hinchliffe | A61F 2/2475 623/1.24 |
| 8,211,165 B1 | 7/2012 | Mcintosh et al. | |
| 8,246,676 B2 | 8/2012 | Acosta et al. | |
| 8,348,997 B2 * | 1/2013 | Thompson | A61F 2/2418 623/2.1 |
| 8,444,687 B2 | 5/2013 | Pavcnik et al. | |
| 8,470,023 B2 * | 6/2013 | Eidenschink | A61F 2/95 623/1.24 |
| 8,568,477 B2 * | 10/2013 | Lashinski | A61F 2/2427 623/2.38 |
| 8,613,763 B2 | 12/2013 | Pavcnik et al. | |
| 8,663,541 B2 | 3/2014 | Chun et al. | |
| 8,672,997 B2 | 3/2014 | Drasler et al. | |
| 8,834,551 B2 | 9/2014 | McGuckin, Jr. | |
| 8,968,388 B2 * | 3/2015 | Hinchliffe | A61F 2/2475 623/1.24 |
| 9,028,542 B2 | 5/2015 | Hill et al. | |
| 9,370,419 B2 | 6/2016 | Hill et al. | |
| 9,421,083 B2 * | 8/2016 | Eidenschink | A61F 2/95 |
| 9,629,721 B2 | 4/2017 | McKinnis et al. | |
| 9,668,861 B2 | 6/2017 | McGuckin, Jr. | |
| 9,675,457 B2 * | 6/2017 | Khosravi | A61F 2/915 |
| 10,143,554 B2 | 12/2018 | Argentine et al. | |
| 2001/0007956 A1 | 7/2001 | Letac et al. | |
| 2001/0010017 A1 | 7/2001 | Letac et al. | |
| 2001/0011187 A1 | 8/2001 | Pavcnik et al. | |
| 2001/0021872 A1 | 9/2001 | Bailey et al. | |
| 2001/0039450 A1 | 11/2001 | Pavcnik et al. | |
| 2002/0107565 A1 | 8/2002 | Greenhalgh | |
| 2002/0138135 A1 | 9/2002 | Duerig et al. | |
| 2002/0177894 A1 | 11/2002 | Acosta et al. | |
| 2003/0014104 A1 | 1/2003 | Cribier | |
| 2003/0055492 A1 | 3/2003 | Shaolian et al. | |
| 2003/0060875 A1 | 3/2003 | Wittens | |
| 2003/0109924 A1 | 6/2003 | Cribier | |
| 2003/0181974 A1 | 9/2003 | Xie et al. | |
| 2003/0209835 A1 | 11/2003 | Chun et al. | |
| 2003/0225447 A1 | 12/2003 | Majercak et al. | |
| 2003/0236568 A1 | 12/2003 | Hojeibane et al. | |
| 2004/0019374 A1 | 1/2004 | Hojeibane et al. | |
| 2004/0034408 A1 | 2/2004 | Majercak et al. | |
| 2004/0093070 A1 | 5/2004 | Hojeibane et al. | |
| 2004/0210301 A1 | 10/2004 | Obermiller | |
| 2004/0215339 A1 | 10/2004 | Drasler et al. | |
| 2004/0236411 A1 | 11/2004 | Sarac et al. | |
| 2004/0254636 A1 | 12/2004 | Flagle et al. | |
| 2005/0021136 A1 | 1/2005 | Xie et al. | |
| 2005/0085900 A1 | 4/2005 | Case et al. | |
| 2005/0137681 A1 | 6/2005 | Shoemaker et al. | |
| 2005/0143807 A1 | 6/2005 | Pavcnik et al. | |
| 2005/0203616 A1 | 9/2005 | Cribier | |
| 2005/0251251 A1 | 11/2005 | Cribier | |
| 2006/0142846 A1 | 6/2006 | Pavcnik et al. | |
| 2006/0190074 A1 | 8/2006 | Hill et al. | |
| 2006/0247762 A1 | 11/2006 | Acosta et al. | |
| 2006/0282157 A1 | 12/2006 | Hill et al. | |
| 2007/0005133 A1 * | 1/2007 | Lashinski | A61F 2/24 623/2.17 |
| 2007/0067021 A1 | 3/2007 | Haverkost et al. | |
| 2007/0129788 A1 | 6/2007 | Drasler et al. | |
| 2007/0276467 A1 | 11/2007 | Kalmann | |
| 2008/0009940 A1 | 1/2008 | Cribier | |
| 2008/0036113 A1 | 2/2008 | Chun et al. | |
| 2008/0077236 A1 | 3/2008 | Letac et al. | |
| 2008/0208329 A1 | 8/2008 | Bishop et al. | |
| 2009/0048662 A1 | 2/2009 | Pavcnik et al. | |
| 2009/0062901 A1 | 3/2009 | McGuckin, Jr. | |
| 2009/0132032 A9 | 5/2009 | Cribier | |
| 2009/0157169 A1 | 6/2009 | Pavcnik et al. | |
| 2010/0005658 A1 | 1/2010 | Haverkost et al. | |
| 2010/0057201 A1 | 3/2010 | Flagle et al. | |
| 2010/0063577 A1 | 3/2010 | Case et al. | |
| 2010/0131049 A1 | 5/2010 | Perkins et al. | |
| 2011/0004295 A1 | 1/2011 | Wittens | |
| 2011/0071625 A1 | 3/2011 | Hill et al. | |
| 2011/0230949 A1 | 9/2011 | Haverkost et al. | |
| 2011/0245916 A1 | 10/2011 | Min et al. | |
| 2011/0319981 A1 | 12/2011 | Hill et al. | |
| 2012/0130468 A1 | 5/2012 | Khosravi et al. | |
| 2013/0317604 A1 | 11/2013 | Min et al. | |
| 2014/0228940 A1 | 8/2014 | McKinnis et al. | |
| 2015/0164642 A1 | 6/2015 | Khosravi et al. | |
| 2015/0209146 A1 | 7/2015 | Hill et al. | |
| 2015/0257885 A1 | 9/2015 | McGuckin, Jr. | |
| 2015/0342738 A1 | 12/2015 | McKinnis et al. | |
| 2016/0250024 A1 | 9/2016 | Hill et al. | |
| 2017/0156863 A1 | 6/2017 | Argentine et al. | |
| 2018/0078372 A1 | 3/2018 | Hill et al. | |
| 2019/0083265 A1 * | 3/2019 | Argentine | A61F 2/2475 |

OTHER PUBLICATIONS

Pavcnik et al., "Percutaneous Management of Chronic Deep Venous Reflux: Review of Experimental Work and Early Clinical Experience with Bioprosthetic Valve," Vascular Medicine, Mar. 2008, 13: 75-84.

Tien et al., "Role of Sinus in Prosthetic Venous Valve," European Journal of Vascular and Endovascular Surgery, vol. 48, Issue 1, pp. 98-104, Jul. 2014.

Us et al., "The Use of External Banding Increases the Durability of Transcommissural External Deep Venous Valve Repair," Eur J Vas Endovasc Surg 33, 494-501 vol. 33, Issue 4, Apr. 2007.

Pavcnik et al., "Percutaneous Autologous Venous Valve Transplantation: Short-Term Feasibility Study in an Ovine Model," Journal of Vascular Surgery, vol. 46, No. 2, Aug. 2007, pp. 338-345.

Extended European Search Report from European Patent Application No. 16201907.9, dated Mar. 29, 2017, 7 pp.

Prosecution History from U.S. Appl. No. 14/958,152 dated Nov. 30, 2017 through Oct. 25, 2018, 68 pp.

(56) References Cited

OTHER PUBLICATIONS

Response to European Search Report dated Mar. 29, 2017, from counterpart European Application No. 16201907.9 filed Dec. 1, 2017, 16 pp.
Examination Report from counterpart European Application No. 16201907.9, dated Nov. 29, 2018, 6 pp.

* cited by examiner

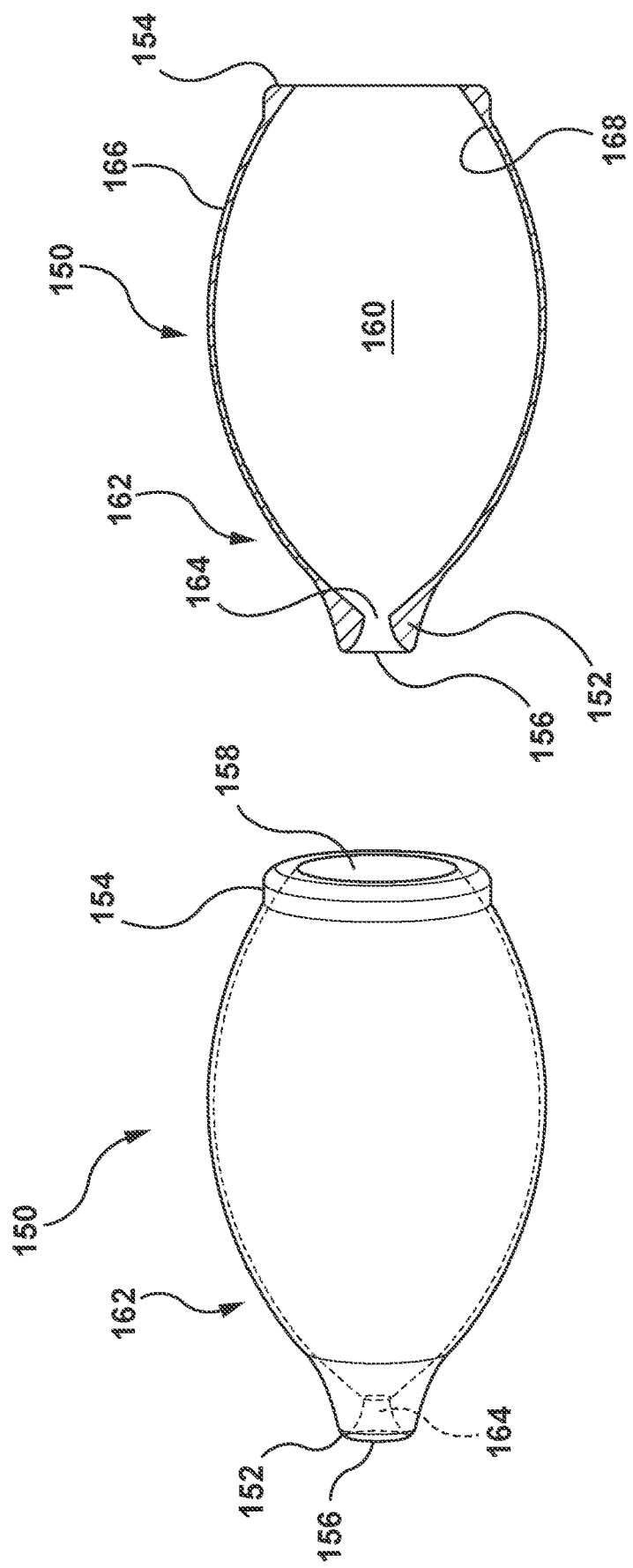

VENOUS VALVE PROSTHESES

This application is a continuation application of U.S. patent application Ser. No. 14/958,152, filed on Dec. 3, 2015, and entitled, "VENOUS VALVE PROSTHESES," the entire content of which is incorporated by reference herein.

FIELD OF THE INVENTION

The following disclosure relates to methods for treating venous valve insufficiency, and more particularly to venous valves prostheses.

BACKGROUND OF THE INVENTION

Venous valves are found within the vasculature of a mammal, particularly the veins. Venous valves prevent the backflow of blood during circulation. For example, venous valves help to fight backflow of blood in the legs caused by gravity pulling the blood away from the heart and back towards the feet of a person when standing. However, when venous valves fail to work properly, blood can flow backwards within the veins and pool in, for example, the legs. Such pooling of blood can cause the veins to become distended, thereby causing the venous valves to fail further. This progressively worsening disorder can lead to varicose veins and chronic venous insufficiency, which is painful and can lead to lower limb ulcerations.

Native venous valves are valves created by thin, overlapping leaflets of tissue that open in response to antegrade pressure, but close in response to retrograde pressure. These valves may be reconstructed in a surgical procedure, but are complicated to reconstruct. Known prosthetic venous valves that attempt to replicate the function of the native leaflet design are complicated to fabricate, may be damaged during percutaneous delivery, and tend to form thrombosis soon after implementation. Accordingly, there is a need for venous valve prostheses which can be delivered percutaneously. There is also a need for a venous valve prosthesis which can prevent thrombosis formation and be delivered to small veins.

BRIEF SUMMARY OF THE INVENTION

The present disclosure provides venous valve prostheses that are easier to fabricate than a thin leaflet design, and are easily delivered percutaneously. Further, the disclosed venous valve prostheses may prevent the formation of thrombus due to the small, continual movement of blood past the prostheses, as well as the prostheses opening and closing along the wall of a vein rather than in the middle of the vein. The venous valve prostheses may include a prosthetic valve disposed on a frame having a valve section and a stabilizing section.

In general in one aspect, the implementation of the disclosure features a venous valve prosthesis including a frame and a prosthetic valve coupled to the frame. The prosthetic valve includes a closed configuration and an open configuration. In the closed configuration, the prosthetic valve is configured such that with the venous valve prosthesis implanted into a vein, an outer surface of the prosthetic valve is in contact with a wall of the vein around a circumference of the prosthetic valve to prevent blood from flowing past the prosthetic valve between the wall of the vein and the outer surface of the prosthetic valve. The prosthetic valve is configured to move to the open configuration such that at least a portion of an outer wall of the prosthetic valve partially collapses away from the wall of the vein in response to antegrade blood flow through the vein to enable blood flow between the outer surface of the prosthetic valve and the wall of the vein.

One or more of the following features may be included. The frame may include a plurality of struts and openings defined between the plurality of struts. In the open configuration, a portion of the prosthetic valve collapses into the openings between the plurality of struts. The openings may be diamond-shaped:

In various embodiments, the frame may include a valve section and a stabilizing section. The prosthetic valve is coupled to the valve section and the stabilizing section is configured to anchor and center the venous valve prosthesis within the vein.

The frame may be a self-expanding frame such that the frame exerts a radially outward force on the prosthesis. The radially outward force is partially overcome by antegrade blood flow to enable the portion of the outer wall of the prosthetic valve to partially collapse inward in response to antegrade blood flow through the vein.

The prosthetic valve may include a tapered surface. The prosthetic valve may further include a substantially cylindrical surface adjacent, a larger end of the tapered surface. In various embodiments, the tapered surface may include notches, and the prosthetic valve is configured to collapse in response to antegrade blood flow at the notches. The notches may extend into the cylindrical surface.

The prosthetic valve may attain the open configuration that enables antegrade blood flow between the prosthetic valve and the wall of the vein in response to a pressure gradient caused by antegrade blood flow being greater than retrograde blood flow, and the prosthetic valve is configured to return to the closed configuration in the absence of the pressure gradient, or when the retrograde blood flow is greater than the antegrade blood flow, to prevent retrograde blood flow between the prosthetic valve and the wall of the vein.

The prosthetic valve may define an opening through a middle portion of the prosthetic valve, wherein the opening is open in both the open configuration and the closed configuration.

In various embodiments, the prosthetic valve may include slits. In some embodiments, in the open configuration the prosthetic valve may partially collapse and the slits are opened to enable antegrade blood flow between the outer surface of the prosthetic valve and wall of the vein upstream of the slits and through the slits. In other various embodiments, the slits may be located on the tapered section of the prosthetic valve, and in the open configuration the slits open in response to the pressure gradient.

In general, in another aspect, the implementation of the disclosure features methods for treating venous valve insufficiency. The method may include delivering a venous valve prosthesis to a site in a vein, wherein the venous valve prosthesis includes a frame and a prosthetic valve. The method further includes deploying the venous valve prosthesis at the site in the vein. The venous valve prosthesis includes a pre-set closed configuration and an open configuration. In the preset closed configuration, the prosthetic valve is in contact with a wall of the vein around a circumference of the prosthetic valve to prevent blood from flowing past the prosthetic valve between the wall of the vein and the outer surface of the prosthetic valve. The prosthetic valve is configured to move to the open configuration such that at least a portion of an outer wall of the prosthetic valve partially collapses away from the wall of the vein in response to antegrade blood flow through the vein to enable blood flow between the outer surface of the prosthetic valve and the wall of the vein.

One or more of the following features may be included. In various embodiments, the step of delivering the venous valve prosthesis to the site in the vein comprises transluminally delivering the venous valve prosthesis to the site. In various embodiment, the venous valve prosthesis may be in a radially compressed delivery configuration during the delivering step, and the step of deploying the venous valve prosthesis may include expanding the venous valve prosthesis to a radially expanded deployed configuration. In some embodiments, the frame is self-expanding and the step of expanding the venous valve prosthesis includes releasing the frame from a sheath such that the frame self-expands to exert a radially outward force on the prosthetic valve such that prosthetic valve contacts the wall of the vein. In other embodiments, the frame is balloon-expandable and the step of expanding the venous valve prosthesis includes inflating a balloon disposed within the frame to expand the frame to exert a radially outward force on the prosthetic valve such that prosthetic valve contacts the wall of the vein.

In embodiments, the prosthetic valve attains the open configuration that enables antegrade blood flow between the prosthetic valve and the wall of the vein in response to a pressure gradient caused by antegrade blood flow being greater than retrograde blood flow, and the prosthetic valve returns to the pre-set closed configuration in the absence of the pressure gradient, or when the retrograde blood flow is greater than the antegrade blood flow, to prevent retrograde blood flow between the prosthetic valve and the wall of the vein.

In various embodiments, the prosthetic valve may define an opening through a middle portion of the prosthetic valve, and the opening is open in both the open configuration and the pre-set closed configuration.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 3 is a schematic illustration of an embodiment of a prosthetic valve of the venous valve prosthesis of FIG. 1.

FIG. 4 is a schematic cross-sectional view of the prosthetic valve of FIG. 3.

DETAILED DESCRIPTION OF THE INVENTION

Figure 1:
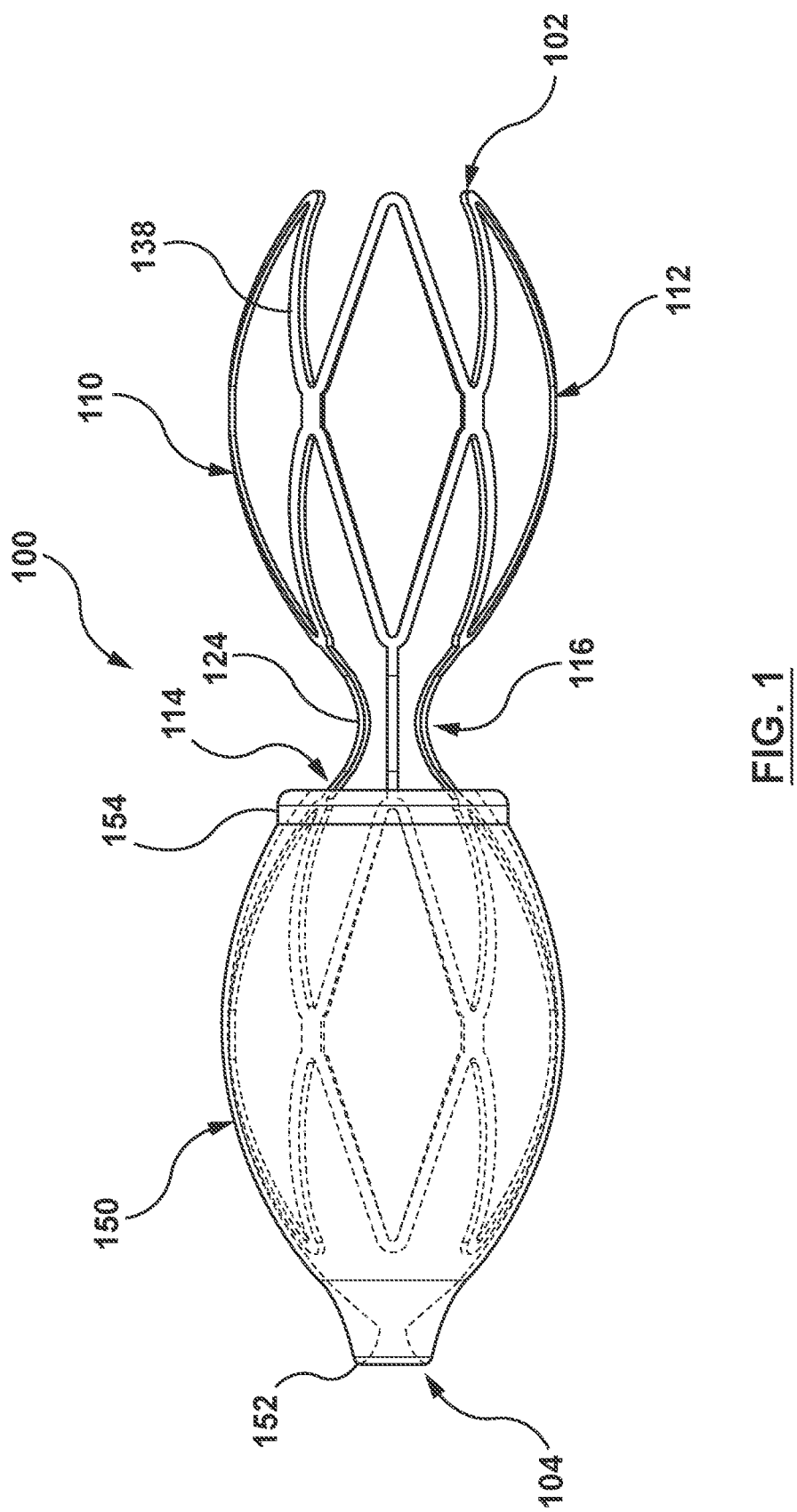
FIG. 1 is a schematic illustration of an embodiment of a venous valve prosthesis.

Specific embodiments of the present invention are now described with reference to the figures, wherein like reference numbers indicate identical or functionally similar elements. The terms "distal" and "proximal" when used in the following description to refer to the venous valve prosthesis are with respect to blood flow in a vein. Thus, the terms "distal" and "distally" refer to the downstream direction of blood flow. In a vein, the downstream direction is towards the heart. Similarly, the terms "proximal" and "proximally" refer to the upstream direction. The terms "downstream" and "upstream" may be used interchangeably with "distal" and "proximal", respectively. Similarly, the term "antegrade" refers to blood flow in the downstream direction (i.e., towards the heart) and the term "retrograde" refers to blood flow in the upstream direction (i.e., away from the heart). The terms "proximal" and "distal" when referring to a delivery device are with respect to a position or direction relative to the treating clinician. Thus, "distal" and "distally" refer to positions distant from or in a direction away from the clinician and "proximal" and "proximally" refer to positions near or in a direction toward the clinician.

Embodiments herein are directed to a venous valve prosthesis having a frame and prosthetic valve coupled to the frame. The venous valve prosthesis includes a closed configuration and an open configuration. With the venous valve prosthesis implanted in a vein and in the closed configuration, an outer surface of the prosthetic valve contacts a wall of the vein around a circumference of the prosthetic valve to prevent blood from flowing past the prosthetic valve between the wall of the vein and the outer surface of the prosthetic valve. With the venous valve prosthesis implanted in a vein and in the open configuration, at least a portion of the outer surface of the prosthetic valve partially collapses away from the wall of the vein in response to antegrade blood flow through the vein to enable blood flow between the outer surface of the prosthetic valve and the wall of the vein. The shear stress of the blood flow over the surface of the prosthetic valve and between the prosthetic valve and the vein wall will help retard the formation of thrombus by keeping the surface of the prosthetic valve and the vein wall clean, or at least cleaner than prosthetic valves that open from the middle of the prosthesis.

Blood flow in the venous system can be caused by movement of muscles, such as from the ankle, calf and thigh muscles, which create antegrade blood flow, or the weight of the blood and the capacitance of the venous system, which creates retrograde blood flow. The venous valve prosthesis is configured to open in the presence of antegrade flow, which may cause a pressure gradient with a higher pressure on an upstream side of the venous valve prosthesis and a lower pressure on a downstream side of the venous valve prosthesis. Conversely, when the retrograde blood flow exceeds the antegrade flow, or the pressure from the antegrade flow and retrograde flow are equal (i.e., no pressure gradient), the venous valve prosthesis is configured to close against the vein wall. Further, a prosthetic valve of the venous valve prosthesis may be configured to be further urged against the vein wall in the presence of retrograde flow. For example, the thickness and material of the prosthetic valve may be selected so as to enable the prosthetic valve to fill and inflate in response to retrograde blood flow, which will further urge the venous valve prosthesis against the vein wall to prevent retrograde blood flow past the venous valve prosthesis.

Figure 18:
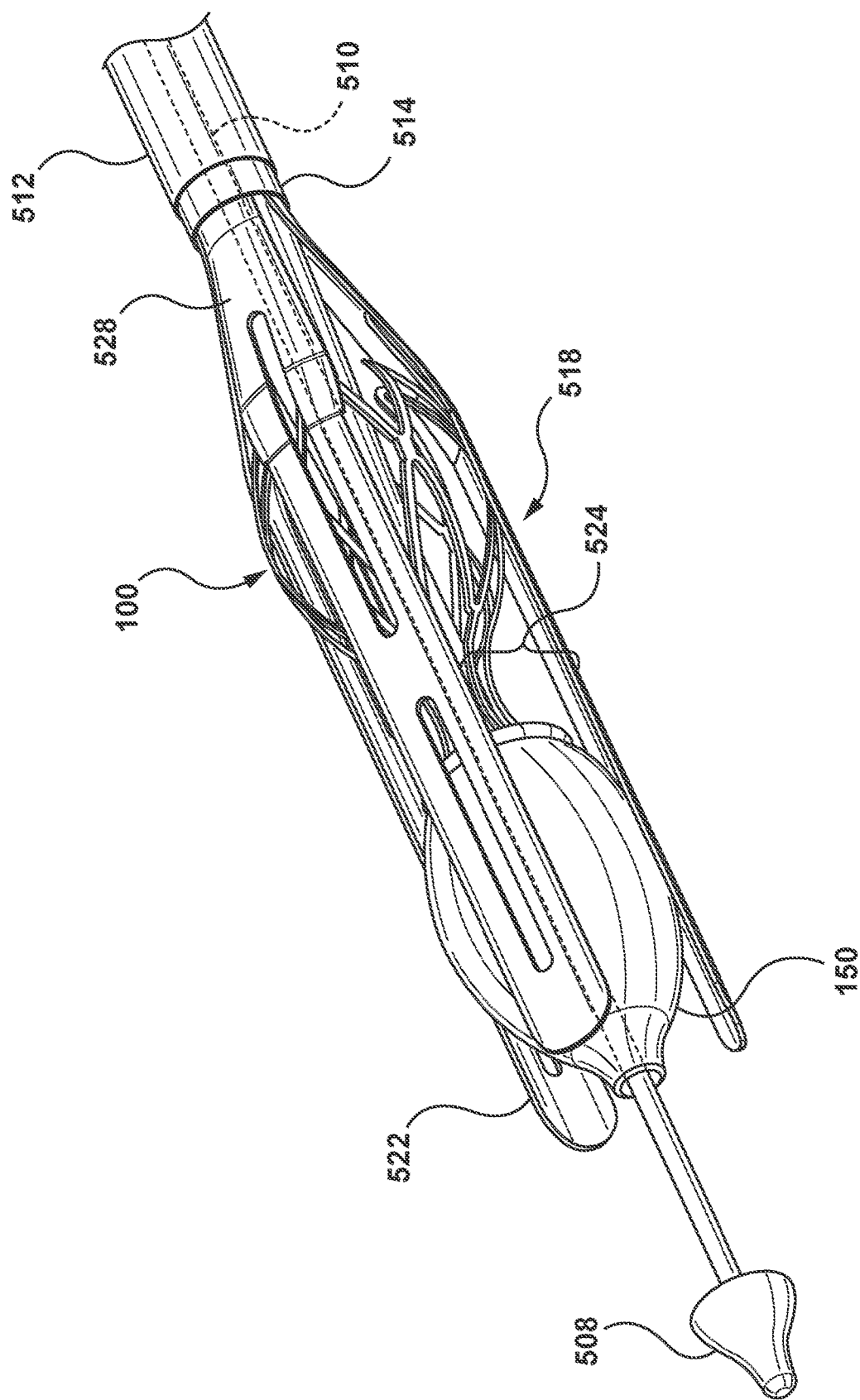
FIG. 18 is a schematic illustration of the delivery device of FIG. 17 with the sheath retracted.

FIG. 18 show a venous valve prosthesis 100 in accordance with an exemplary embodiment hereof. The venous valve prosthesis 100 includes an upstream end 104 and a downstream end 102. The venous valve prosthesis 100 includes a frame 110 and a prosthetic valve 150 coupled to the frame 110. In the embodiment of FIG. 18 the prosthetic valve 150 is coupled to an outer surface of the frame 110, but it could alternatively be coupled to an inner surface of the frame 110.

Figure 2:
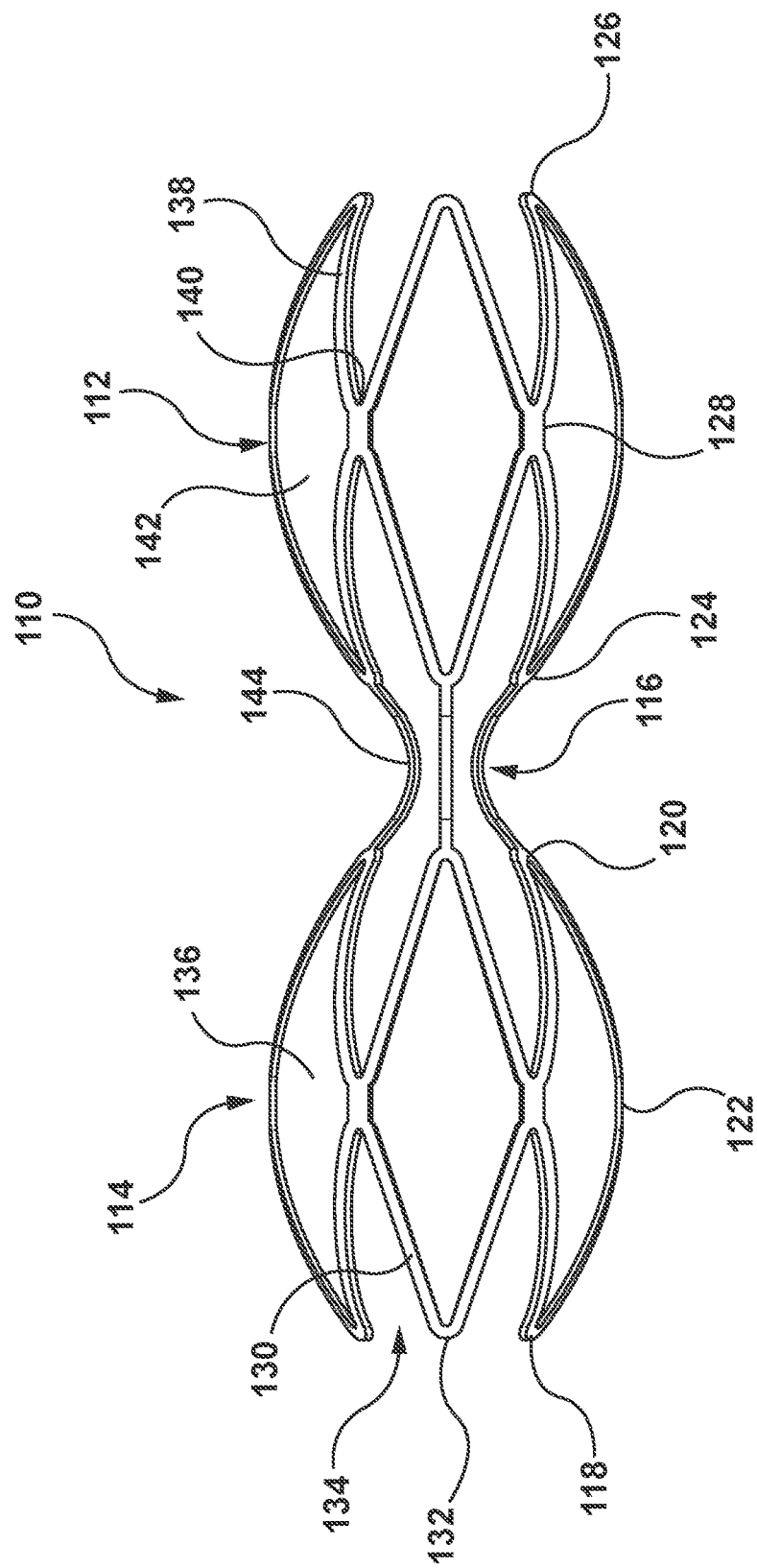
FIG. 2 is a schematic illustration of an embodiment of a frame of the venous valve prosthesis of FIG. 1.

The frame 110 is shown without the valve prosthesis 150 in FIG. 2 for clarity. FIG. 2 shows the frame 110 in a radially expanded deployed configuration. The frame 110 may also be crimped into a radially contracted delivery configuration, as explained in more detail below. The frame 110 is a support structure for maintaining the venous valve prosthesis 100 in a desired location in a vein, as explained in more detail below. The frame 110 may also be referred to as a stent. As shown in FIGS. 1-2, the frame 110 may have an hourglass shape including a valve section 114, a stabilizing section 112, and a connecting section 116 coupling the valve section 114 to the stabilizing section 112. Although the valve section 114, the stabilizing section 112, and the connecting section 116 are described separately, they may be formed of unitary structure or may be formed separately and attached to each other. Further, in an alternative embodiment, the valve section 114 and the stabilizing section 112 may be joined directly together without the connecting section 116.

The valve section 114 of the frame 110 includes an upstream end 118, and downstream end 120, and a central portion 122. As can be seen in FIG. 2, in the radially expanded deployed configuration, the upstream end 118 and the downstream end 120 each have a smaller diameter than the central portion 122. Thus, the central portion 122 of the valve section 114 of the frame 110 bulges outwardly relative to the upstream end 118 and the downstream end 120. Similarly, the stabilizing section 112 includes an upstream end 124, a downstream end 126, and a central portion 128. As with the valve section 114, in the radially expanded deployed configuration, the upstream end 124 and the downstream end 126 each have a smaller diameter than the central portion 128. Thus, the central portion 128 of the stabilizing section 112 of the frame 110 bulges outwardly relative to the upstream end 124 and the downstream end 128.

The valve section 114 of the frame 110 includes a plurality of struts 130 connected by bends 132 and formed into a general tubular shape defining a lumen 134 therewithin. The struts 130 and the bends 132 define openings 136 therebetween. In the embodiment shown in FIGS. 1-8, the openings 136 are generally diamond-shaped. However the openings 136 are not required to be diamond shaped. The openings 136 are sized and shaped to enable the prosthetic valve 150 to depress into the openings 136, as described in more detail below.

In the embodiment shown, the stabilizing section 112 of the frame 110 is identical to the valve section 114. Thus the stabilizing section 112 includes a plurality of struts 138 connected by bends 140 and formed into a generally tubular shape, as explained above. The struts 138 and the bends 140 define openings 142 therebetween. In the embodiment shown in FIGS. 1-8, the openings 142 are generally diamond-shaped. However, the openings 142 are not required to be diamond shaped. Further, in other embodiments, the stabilizing section 112 and the valve section 114 are not identical. For example, the configurations of the struts 138 and the bends 140 of the stabilizing section may be different than the struts 130 and the bends 132 of the valve section 114. In still other embodiments, the stabilizing section 112 and the valve section 114 may be configured similarly but one section may be larger, either in diameter, length or both, than the other (e.g., the stabilizing section 112 may be larger than the valve section 114).

The connecting section 116 of the frame 110 includes a plurality of struts 144 connecting the downstream end 120 of the valve section 114 to the upstream end 124 of the stabilizing section 112.

Although the frame 110 has been described in parts, the frame 110 can be constructed as a single, unitary piece, or the frame 110 may be constructed as separate pieces and joined together, such as by welding, fusion, adhesives, or mechanical attachment. The struts 130, 138, 144 and bends 132, 140 of the frame 110 may be made of materials generally known for use in stents. For example, and not by way of limitation, the frame 110 may be made from materials commonly used for stents, such as stainless steel, Nitinol (nickel-titanium shape memory alloy), Elgiloy® (cobalt-chromium-nickel alloy), some biocompatible plastics, as well as combinations thereof. The frame 110 may be self-expanding or may be balloon expandable.

The frame 110 may include other features not shown. For example, and not by way of limitation, the frame 110 may include barbs or hooks to assist in holding the frame 110 in the desired location in a vein. In particular, stabilizing section 112 may include such barbs or hooks.

As shown in FIG. 1, the prosthetic valve 150 is coupled to the valve section 114 of the frame 110. The prosthetic valve 150 may be coupled to the frame 110 by any suitable method, such as a friction fit, mechanical connection such as sutures, an adhesive connection, or other connections. FIGS. 3-4 show the prosthetic valve 150 separated from the frame 110 for clarity. The prosthetic valve 150 includes an upstream end 152 and a downstream end 154. The prosthetic valve 150 may be a thin layer of material defining a conduit 160 therethrough. The upstream end 152 includes an upstream opening 156 and the downstream end 154 includes a downstream opening 158 defining upstream and downstream ends of the conduit 160, respectively. As shown in FIGS. 3-4, an upstream portion 162 of the prosthetic valve 150 is tapered such that the upstream opening 156 is smaller than the downstream opening 158. The tapered configuration may help provide a smooth transition for the blood flow so as to minimize, or eliminate, the creation of turbulent flow. The size of the upstream and downstream openings will depend on the size of the vessel into which the venous valve prosthesis is deployed. In a non-limiting example, the upstream opening 156 may be in the range of 0.050-0.080 inches (1.27-2.03 mm) in diameter and the downstream opening may be in the range of 0.217-0.453 inches (5.5-11.5 mm) in diameter with the venous valve prosthesis 100 in the radially expanded configuration. In the embodiment shown, the conduit 160 may include a constriction 164 adjacent the upstream opening 156. The constriction 164 narrows the diameter of the conduit 160. The diameter of the constriction may depend on the vessel into which the venous valve prosthesis is deployed. In a non-limiting example, the diameter at the constriction 164 may be in the range of 0.016-0.050 inches (0.406-1.27 mm).

The prosthetic valve 150 includes an outer surface 166 and an inner surface 168. The thickness of the prosthetic valve 150 may be in the range of 0.007-0.016 inches (0.178-0.406 mm). The prosthetic valve 150 may be made from, for example silicone, ePTFE, or any other biocompatible flexible material.

Figure 5:
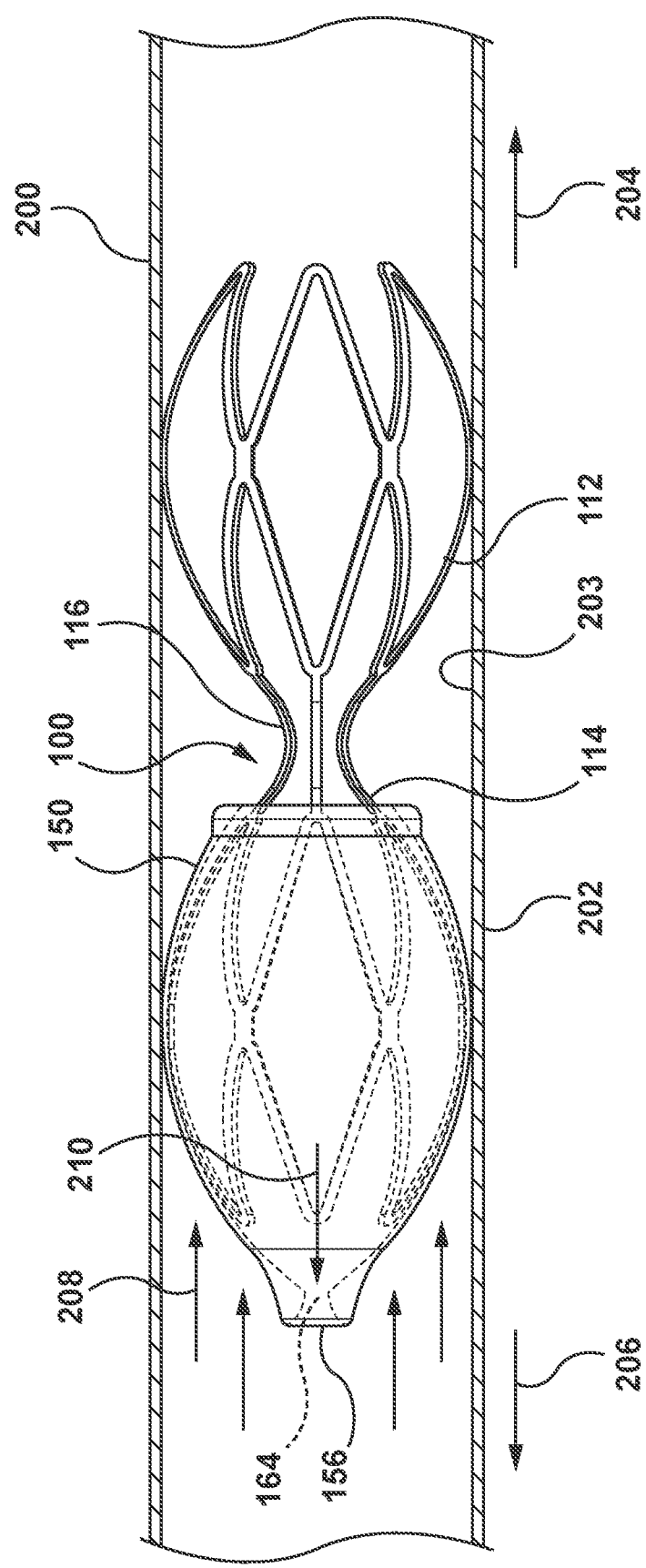
FIG. 5 is a schematic illustration, of the venous valve prosthesis of FIG. 1 deployed in a vein in a closed configuration.

FIG. 5 shows the venous valve prosthesis 100 implanted into a vein 200 in the radially expanded configuration and the prosthetic valve 150 in a closed configuration. The vein 200 may be any vein. However, the venous, valve prosthesis 100 is particularly suited to be implanted into the veins in the leg. For example, and not by way of limitation, the vein 200 may be the greater or lesser saphenous veins, the anterior or posterior tibial veins, popliteal veins, and femoral veins. In FIG. 5, the arrow 204 represents the downstream or antegrade direction (towards the heart) and the arrow 206 represents the upstream or retrograde direction (away from the heart).

In the radially expanded configuration, the valve section 114 of the frame 110 pushes the prosthetic valve 150 radially outward and into contact with an inner surface 203 of a wall 202 of the vein 200. Accordingly, blood flow 208 in the retrograde direction is blocked between the outer surface 166 of the prosthetic valve 150 and the inner surface 203 of the wall 202. This closed configuration shown in FIG. 5 occurs when the pressure gradient in the vein 200 is zero or approaching zero, for example less than 2 mm Hg, and thus not attempting to push blood in the antegrade direction, or when the blood flow 208 is moving in the upstream direction 206.

However, even, in the closed configuration, the constriction 164 and the upstream opening 156 of the prosthetic valve 150 enable a small amount of flow in the retrograde direction, as shown by arrow 210 in FIG. 5, or even in the antegrade direction if there is some blood movement in the upstream direction 206. As explained above, a potential deficiency with existing venous valve prostheses is the development of thrombosis on the venous valve prosthesis. It is believed that this small amount of flow during periods in which the pressure gradient is lower, for example, when a person is sleeping, assists in preventing thrombosis on the prosthetic valve 150. However, larger retrograde flow is prevented by the blood filling the conduit 160 of the prosthetic valve 150, which exerts and outward force on the inner surface 168 of the prosthetic valve 150, thus further moving the prosthetic valve to the closed position.

Figure 6:
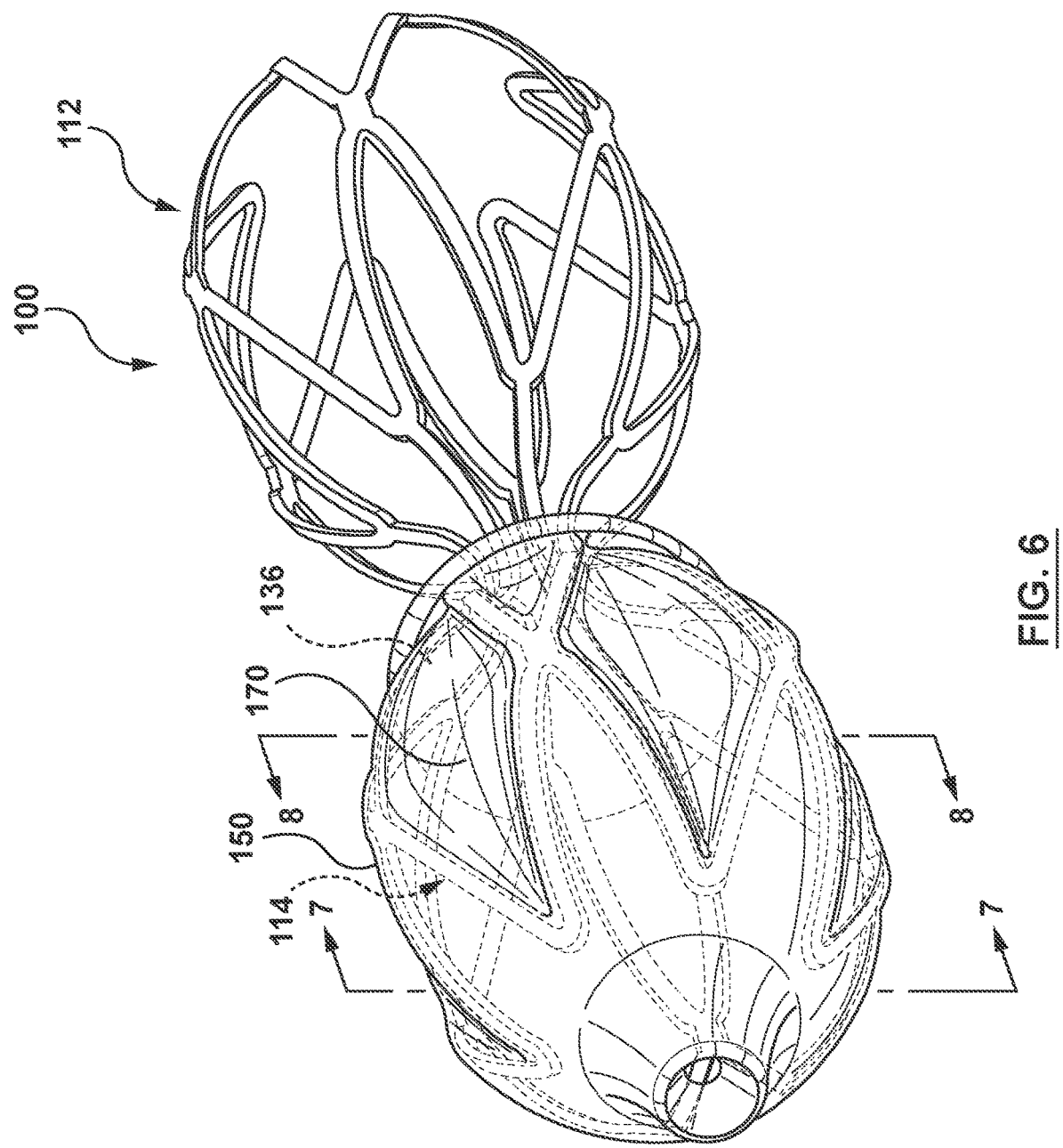
FIG. 6 is a schematic illustration of the venous valve prosthesis of FIG. 1 in an open configuration.
Figure 8:
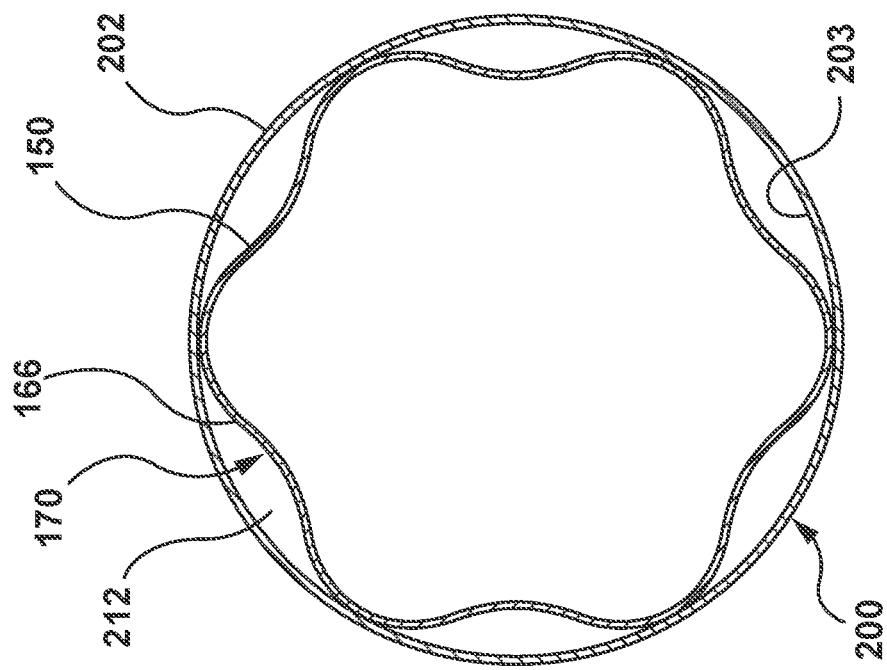
FIG. 8 is a schematic cross-sectional view of the venous valve prosthesis of FIG. 1 deployed in a vein in an open configuration with the frame removed for clarity.
Figure 7:
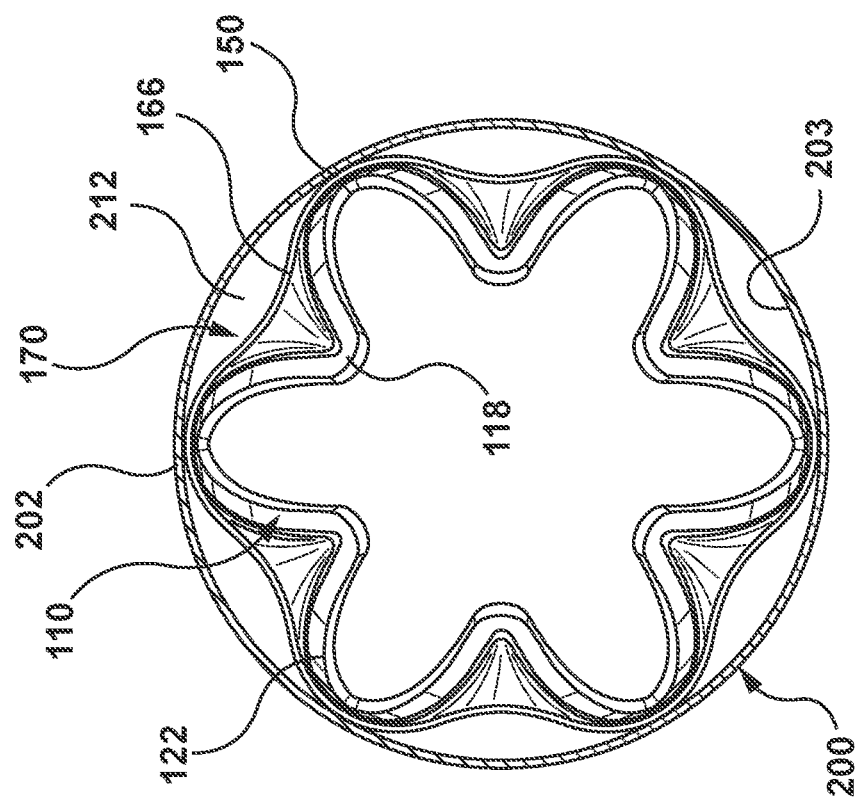
FIG. 7 is a schematic cross-section end view of the venous valve prosthesis of FIG. 1 deployed in a vein in an open configuration.

When pressure is exerted to push blood flow 208 in the downstream direction 204, such as by action of the skeletal-muscle pump, the outer surface 166 of the prosthetic valve 150 at least partially collapses away from the inner surface 203 of the wall 202. For example, the prosthetic valve may be configured to at least partially collapse when the pressure gradient is at least 2 mm Hg. FIGS. 6-8 show schematically the prosthetic valve 150 partially collapsing away from the inner surface 203 of the wall 202 such that a gap 212 forms between the outer surface 166 of the prosthetic valve 150 and the inner surface 203 of the wall 202. In the embodiment of FIGS. 1-8, the prosthetic valve 150 partially collapses by depressing into the openings 136 formed between the struts 130 and the bends 132 of the valve section 114 of the frame 110, as described above. Accordingly, depressions 170 are formed in the prosthetic valve 150 at the openings 136. Thus, the gaps 212 formed between the outer surface 166 of the prosthetic valve 150 and the inner surface 203 of the wall 202 enable blood flow 208 in the downstream direction 204 between the outer surface 166 of the prosthetic valve 150 and the wall 202.

FIG. 7 shows a schematic cross-section end view of the venous valve prosthesis 100 as seen from the section line 7-7 in FIG. 6. As seen in FIG. 7, the upstream end 118 of the valve section 114 of the frame 110 is spaced from the wall 202. This is due to the upstream end 118 being a smaller diameter than the central portion 122 of the valve section 114, and thus smaller in diameter than the vein 200. Thus, blood can flow over the upstream end 118 of the valve section 114 and the upstream portion 162 of the prosthetic valve 150. At the central portion 122 of the valve section 114, the struts remain adjacent to the inner surface 203 of the wall 202, with the prosthetic valve 150 therebetween. However, in the openings 136, the prosthetic valve 150 collapses from the pressure exerted to form depressions 170, thereby forming the gap 212 between the outer surface 166 of the prosthetic valve 150 and the inner surface 203 of the wall 202. FIG. 8 shows a cross-sectional view at the central portion 122 with the frame 110 removed for clarity.

Although the embodiment of FIGS. 1-8 shows that the valve section 114 of the frame 110 does not compress in reaction to pressure exerted to push blood in the downstream direction, the valve section 114 of the frame 110, or a portion of the valve section 114, may be constructed to radially compress in reaction to this pressure. Such a compression may create a gap around the entire circumference of the prosthetic valve 150 between the outer surface 166 of the prosthetic valve 150 and the inner surface 203 of the vein wall 202. In such an embodiment, the stabilizing section 112 of the frame 110 does not radially compress and therefore prevents the venous valve prosthesis 100 from migrating within the vein 200.

FIGS. 9-14 show a venous valve prosthesis 300 according to another exemplary embodiment hereof. The venous valve, prosthesis 300 includes an upstream end 304 and a downstream end 302. The venous valve prosthesis 300 includes a frame 310, a prosthetic valve 350, and a nosepiece 380 coupling the prosthetic valve 350 to the frame 310. In the embodiment of FIGS. 9-12 the prosthetic valve 350 is coupled to an outer surface of the frame 310, but it could alternatively be coupled to an inner surface of the frame 310.

Figure 9:
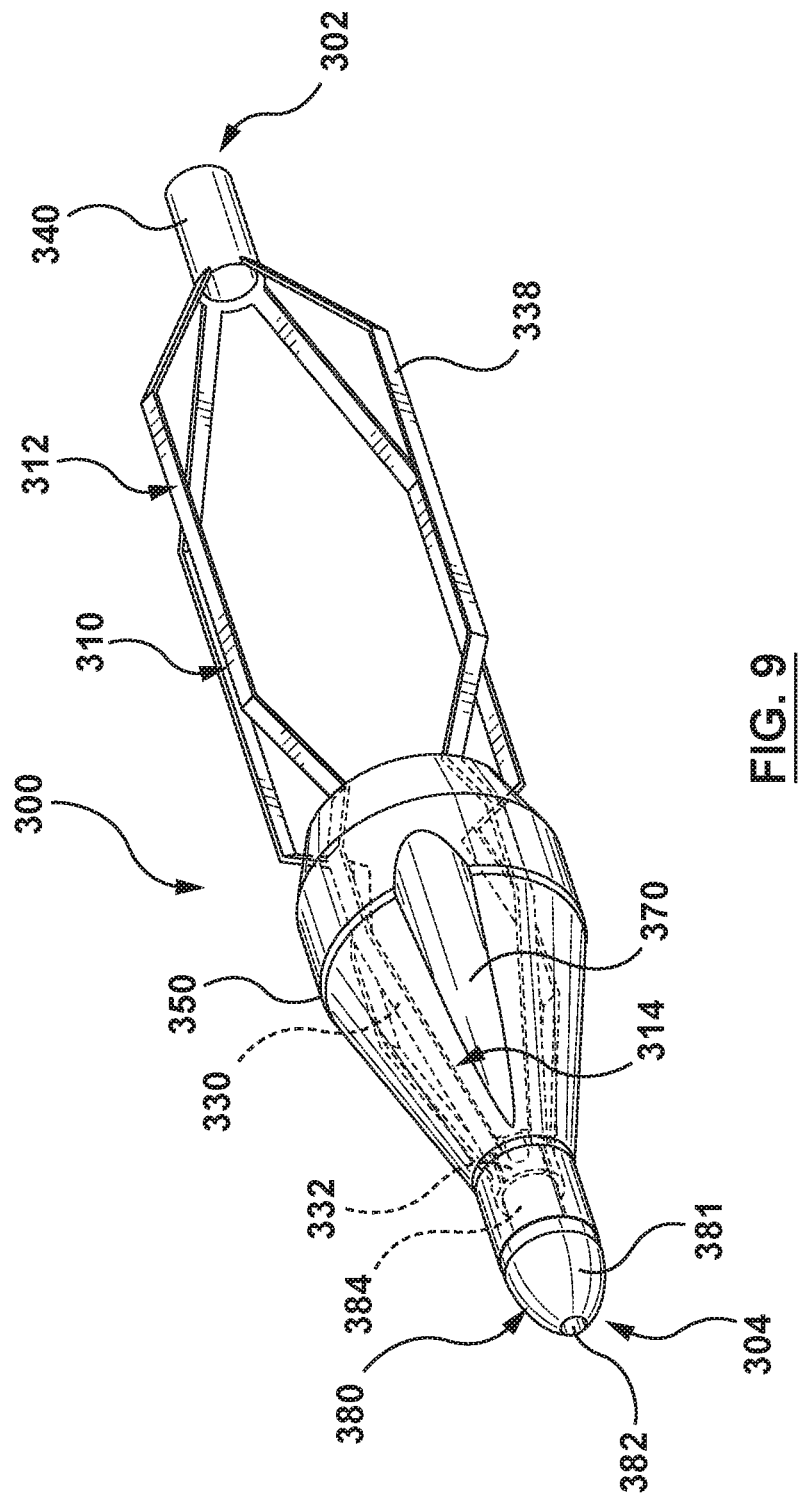
FIG. 9 is a schematic illustration of a venous valve prosthesis according to another embodiment hereof.
Figure 10:
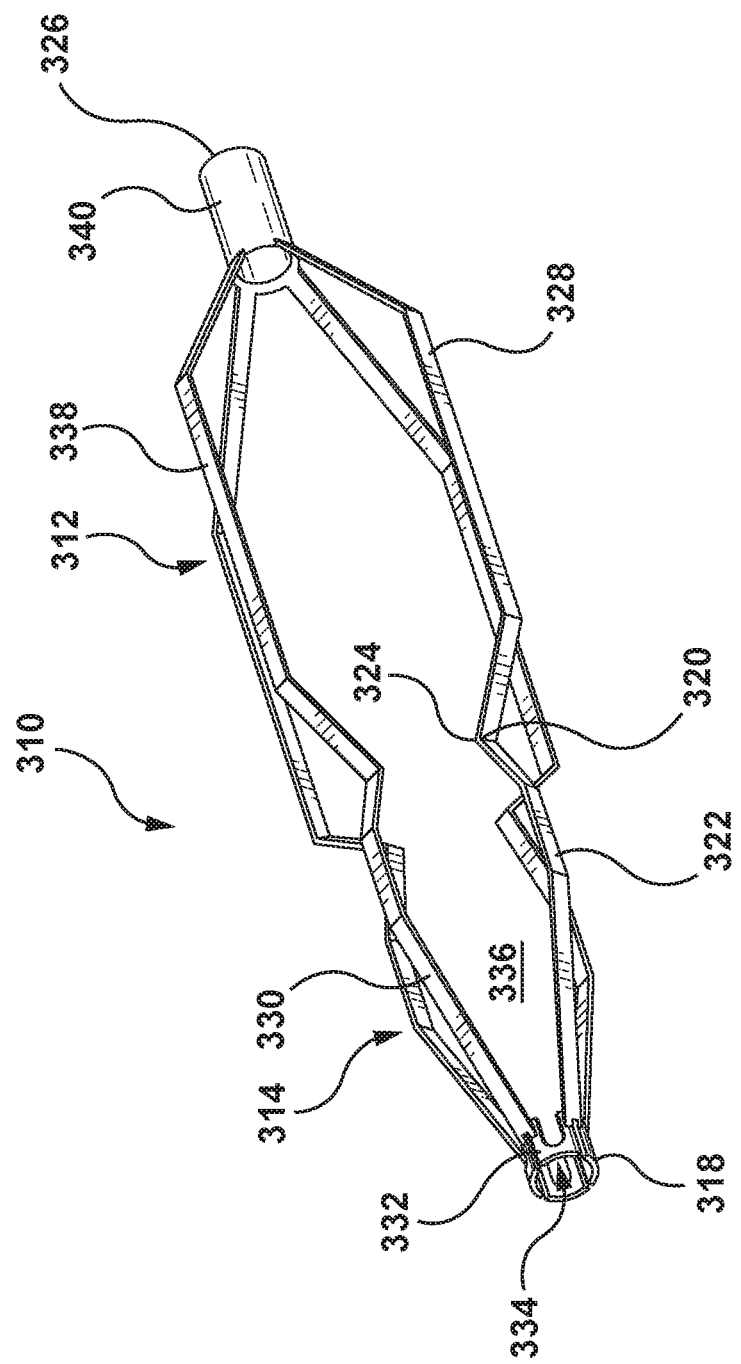
FIG. 10 is a schematic illustration of an embodiment of a frame of the venous valve prosthesis of FIG. 9.

The frame 310 is shown without the valve prosthesis 350 in FIG. 10 for clarity. FIG. 10 shows the frame 310 in a radially expanded deployed configuration. The frame 310 may also be crimped into a radially compressed delivery configuration, as explained in more detail below. The frame 310 is a support structure for maintaining the venous valve prosthesis 300 in a desired location in a vein, as explained in more detail below. The frame 310 may also be referred to as a stent. As shown in FIGS. 9-10, the frame 310 includes a valve section 314 and a stabilizing section 312 coupled to the valve section 314. Although the valve section 314 and the stabilizing section 312 are described separately, they may be formed of unitary structure or may be formed separately and attached to each other.

The valve section 314 of the frame 310 includes an upstream end 318, a downstream end 320, and a central portion 322. As can be seen in FIG. 10, in the radially expanded deployed configuration, the upstream end 318 and the downstream end 320 each may have a smaller diameter than the central portion 122. Similarly, the stabilizing section 312 includes an upstream end 324, a downstream end 326, and a central portion 328. As with the valve section 314, in the radially expanded deployed configuration, the upstream end 324 and the downstream end 326 each may have a smaller diameter than the central portion 328.

The valve section 314 of the frame 310 includes a plurality of struts 330 connected at or adjacent to the upstream end 318 by a hub 332 and formed into a generally tubular shape defining a lumen 334 therewithin. The struts 330 define openings 336 therebetween. In the embodiment shown in FIGS. 9-12, the downstream ends of the struts 330 are not connected to each other. However, in other embodiments, the downstream ends of the struts 330 may be connected. The stabilizing section 312 of the frame 310 includes a plurality of struts 338 connected at a downstream end by a hub 340. The struts 338 define openings 342 therebetween. In the embodiment shown in, FIGS. 9-12, the upstream end 324 of the stabilizing section 312 is connected to the downstream end 320 of the valve section 314.

Although the frame 310 has been described in parts, the frame 310 may be constructed as a single, unitary piece or the frame 310 may be constructed as separate pieces and joined together by any suitable means, such as by welding, fusion, adhesives, or mechanical attachment. The struts 330, 338 and hubs 332, 340 of the frame 310 may be made of materials generally known for use in stents. For example, and not by way of limitation, the frame 310 may be made from materials commonly used for stents, such as stainless steel, Nitinol (nickel-titanium shape memory alloy), Elgiloy® (cobalt-chromium-nickel alloy), some biocompatible plastics, as well as combinations thereof. The frame 310 may be self-expanding or may be balloon expandable.

The frame 310 may include other features not shown. For example, and not by way of limitation, the frame 310 may include barbs or hooks to assist in holding the frame 310 in the desired location in a vein. In particular, stabilizing section 312 may include such barbs or hooks.

Figures 11, 12:
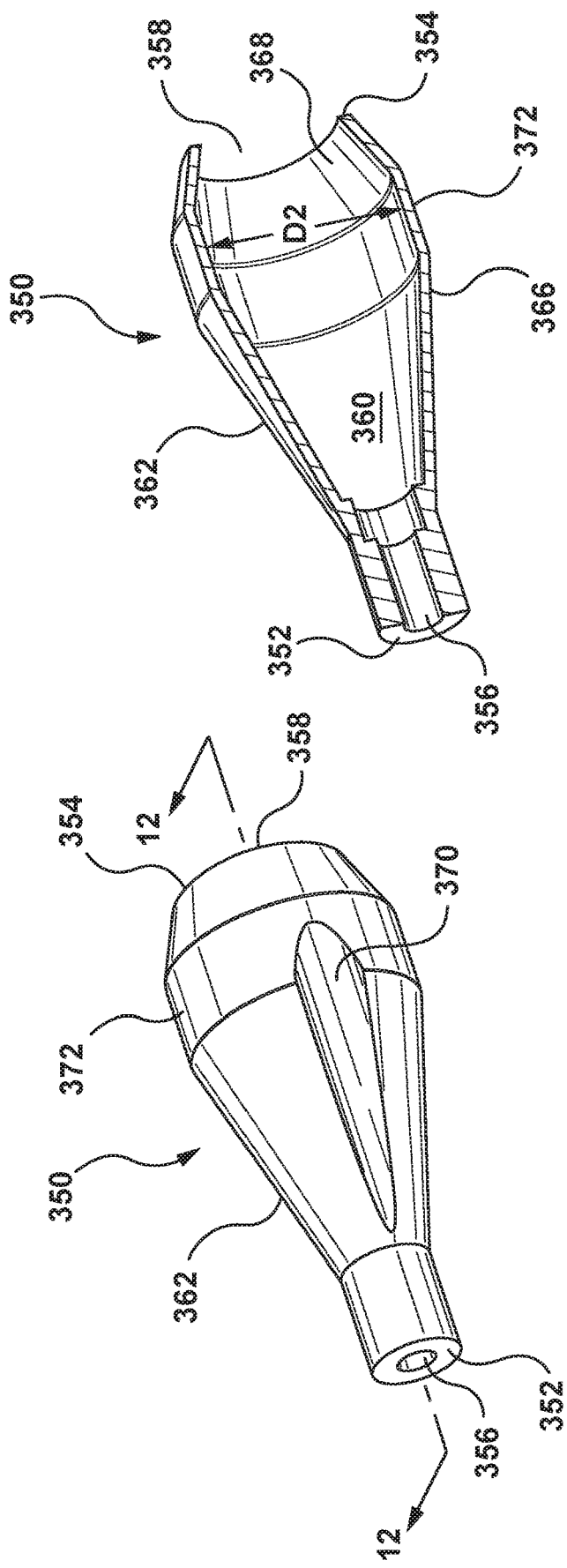
FIG. 11 is a schematic illustration of an embodiment of a prosthetic valve of the venous valve prosthesis of FIG. 9.
FIG. 12 is a schematic cross-sectional view of the prosthetic valve of FIG. 11.

As shown in FIG. 9, the prosthetic valve 350 is coupled to the valve section 314 of the frame 310. FIGS. 11-12 show the prosthetic valve 350 separated from the frame 310 for clarity. The prosthetic valve 350 includes an upstream end 352 and a downstream end 354. The prosthetic valve 350 is a thin layer of material defining a conduit 360 therethrough. The upstream end 352 includes an upstream opening 356 and the downstream end 354 includes a downstream opening 358 defining upstream and downstream ends of the conduit 360, respectively. As shown in FIGS. 11-12, the prosthetic valve 350 includes a tapered surface 362. The tapered surface 362 may extend from a cylindrical surface 372 towards the upstream end 352 of the prosthetic valve such that a diameter of the conduit 360 at the cylindrical surface 372 is larger than a diameter of the conduit at the upstream end 352. In a non-limiting example, the upstream opening 356 may be in the range of 0.050-0.080 inches (1.27-2.03 mm) in diameter and the diameter D2 of the conduit at the cylindrical surface 372 may be in the range of 0.217-0.453 inches (5.5-11.5 mm) in diameter with the venous valve prosthesis 300 in the radially expanded configuration.

The prosthetic valve 350 shown in FIGS. 9-14 includes a pair of notches 370 extending longitudinally along the tapered surface 362 and partially into the cylindrical surface 372. The notches 370 are disposed diametrically opposed to each other. Although two notches 370 are shown in the embodiment of FIGS. 9-12, more or fewer notches 370 may be utilized. For example, and not by way of limitation, three or four notches 370 may be utilized equally spaced about a circumference of the prosthetic valve 350.

The prosthetic valve 350 includes ah outer surface 366 and an inner surface 368. The thickness of the prosthetic valve 350 may be in the range of 0.007-0.016 inches (0.178-0.406 mm). The prosthetic valve 350 may be made from, for example, silicone, ePTFE, or any other biocompatible flexible material.

Referring back to FIG. 9, the nose-piece 380 may couple the prosthetic valve 350 to the frame 310. As shown in FIG. 9, the nose-piece 380 may include a bulbous nose 381 which abuts against the upstream end 352 of the prosthetic valve 350 and a shaft 384 which is sized to extend through opening 356 at the upstream end 352 of the prosthetic valve 350. The shaft 384 extends through an upstream portion of conduit 360 to a location where the shaft 384 engages the upstream hub 332 of the valve section 314 of the frame 310. The shaft 384 may engage the hub 332 by a friction fit connection, or may include perturbations which match openings in the hub 332. The nose-piece 380 includes a conduit 382 extending therethrough which is in communication with the conduit 360 of the prosthetic valve 350. The conduit 382 may be in the range of 0.016-0.050 inches (0.406-1.27 mm) in diameter.

Although the venous valve prosthesis 300 of FIGS. 9-14 is shown with a nosepiece 380, the venous valve prosthesis 300 may not include a nose-piece 380. For example, and not by way of limitation, the prosthetic valve 350 may taper to the desired size for the upstream opening 356. Further, the prosthetic valve 350 may be coupled to the frame 310 by a friction fit, mechanical connection such as sutures, an adhesive connection, or other connections.

Figure 13:
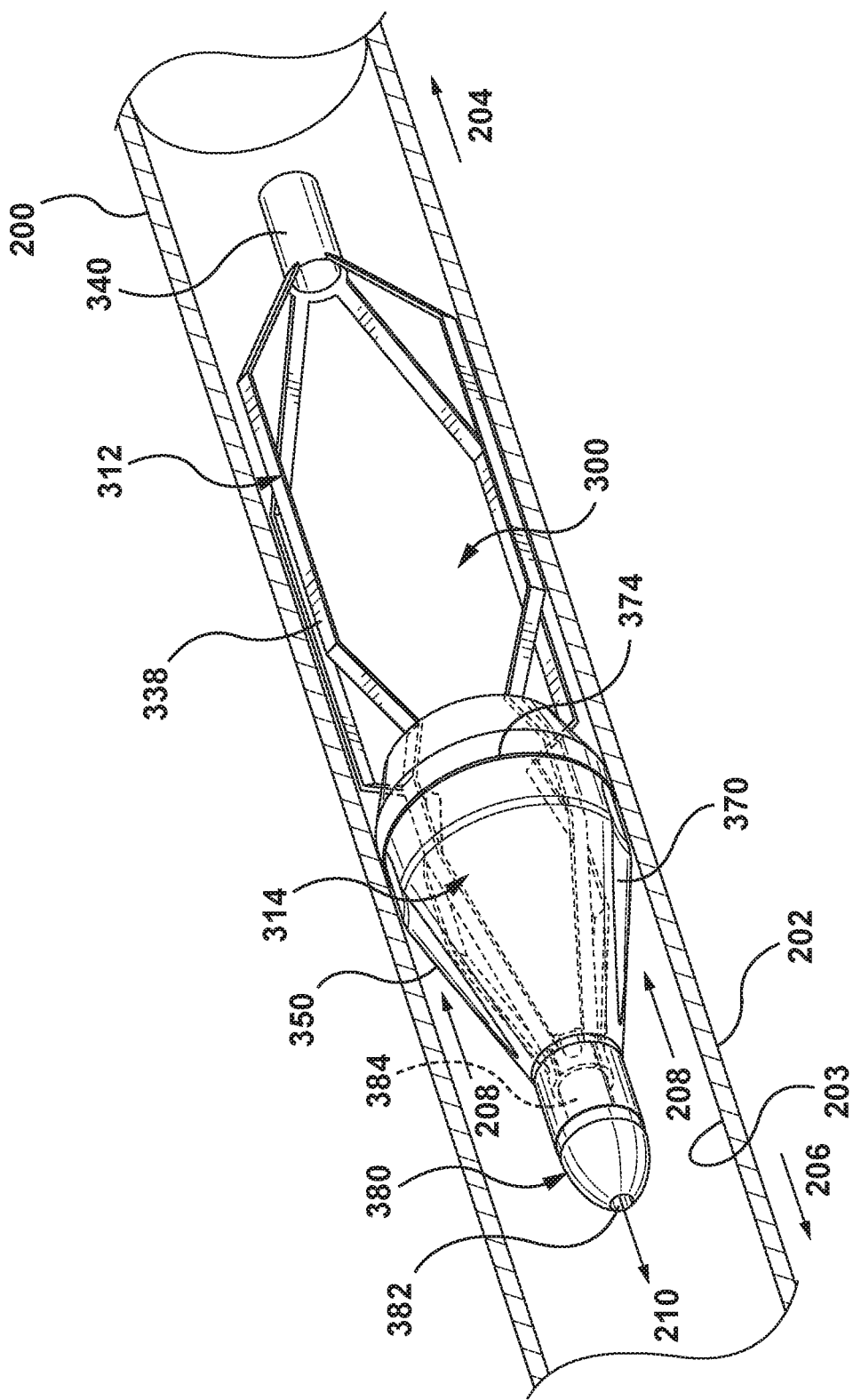
FIG. 13 is a schematic illustration of the venous valve prosthesis of FIG. 9 deployed in a vein in a closed configuration.

FIG. 13 shows the exemplary venous valve prosthesis 300 implanted into the vein 200 in the radially expanded configuration and in a closed configuration. In FIG. 13 the arrow 204 represents the downstream direction (towards the heart) and the arrow 206 represents the upstream direction (away from the heart).

In the radially expanded configuration, the valve section 314 of the frame 310 pushes the prosthetic valve 350 radially outward and in contact with the inner surface 203 of the wall 202 of the vein 200. Accordingly, blood flow 208 in the downstream direction is blocked between the outer surface 366 of the prosthetic valve 350 and the inner surface 203 of the wall 202. This closed configuration shown in FIG. 13 occurs when the vein 200 is relaxed and not attempting to push blood in the downstream direction.

The conduit 382 through the nosepiece 380 in communication with the conduit 360 through prosthetic valve 350 enables a small amount of flow in the upstream direction, as shown by arrow 210 in FIG. 13. As explained above, a potential deficiency with existing venous valve prostheses is the development of thrombosis on the venous valve prosthesis. It is believed that this small amount of flow assists in preventing thrombosis on the prosthetic valve 350.

Figure 14:
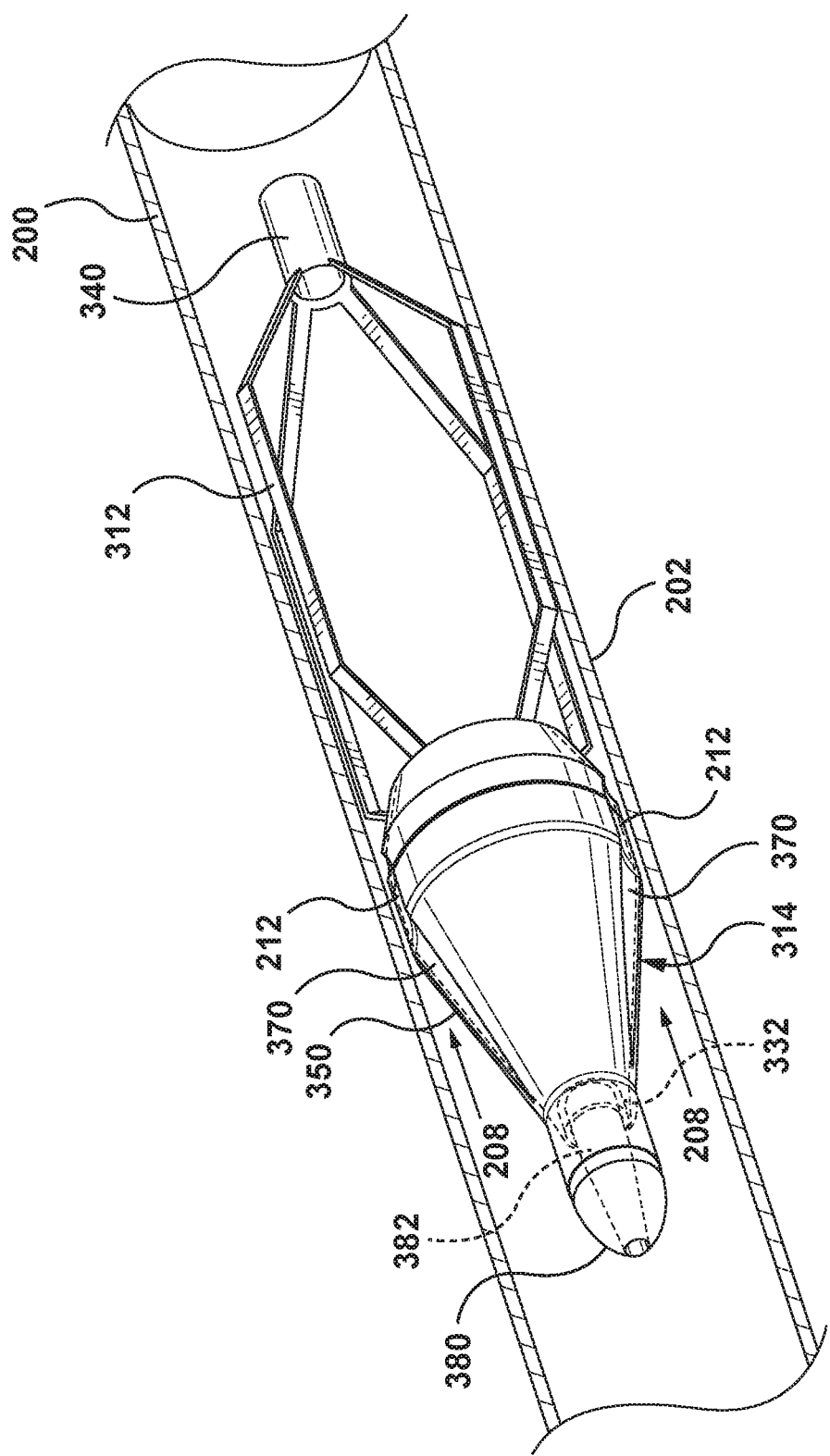
FIG. 14 is a schematic illustration of the venous valve prosthesis of FIG. 9 deployed in a vein in an open configuration.

When pressure is exerted to push blood in the downstream direction 204, the valve section 314 of the frame 310 partially compresses such that the outer surface 366 of the prosthetic valve 350 moves away from the wall 202. FIG. 14 shows schematically at least a portion of the valve section 314 of the frame 310 and the prosthetic valve 350 moving away from the wall 202 such that a gap 212 forms between the outer surface 366 of the prosthetic valve 350 and the inner surface 203 of the wall 202. In the embodiment of FIGS. 9-14, the frame 310 and the prosthetic valve 350 compress away from the wall 202 particularly at the notches 370. However, the notches 370 can be excluded and the entire circumference of the valve section 314 of the frame 310 may compress such that the entire circumference of the prosthetic valve 350 may move away the wall 202. Further, even with notches 370, the entire circumference of the valve section 314 may be configured to compress such that the entire circumference of the prosthetic valve 350 moves away, from the wall 202. Alternatively, the notches 370 may be excluded and the valve section 314 of the frame 310 may be configured such that only a portion of the valve section 314 compresses in response to antegrade flow of blood through the vein 200.

In an alternative embodiment, the frame 310 does not compress. Rather, the notches 370 compress into openings 336 between the struts 330 of the frame 310, as described above with reference to the embodiment of FIGS. 1-8. In such an embodiment, the notches 370 may extend at least partially onto the cylindrical surface 372. Extending the notches 370 at least partially onto the cylindrical surface 372 may create an area of weakness that is more easily compressed due to the pressure gradient.

Accordingly, the gaps 212 formed between the outer surface 366 of the prosthetic valve 350 and the inner surface 203 of the wall 202 enable blood flow 208 in the downstream direction 204 between the outer surface 366 and the wall 202.

Figure 15:
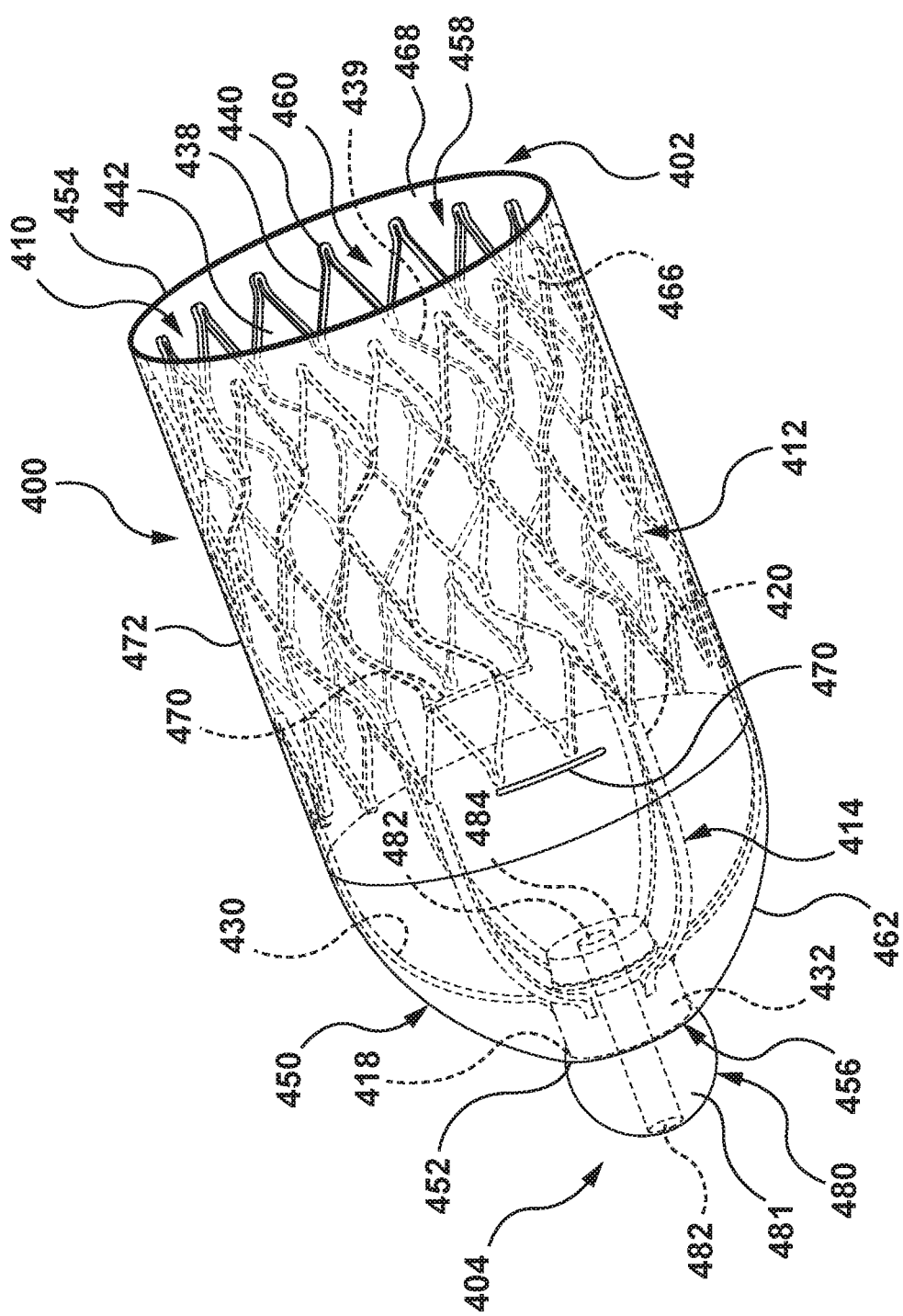
FIG. 15 is a schematic illustration of a venous valve prosthesis according to another embodiment hereof.
Figure 16A:
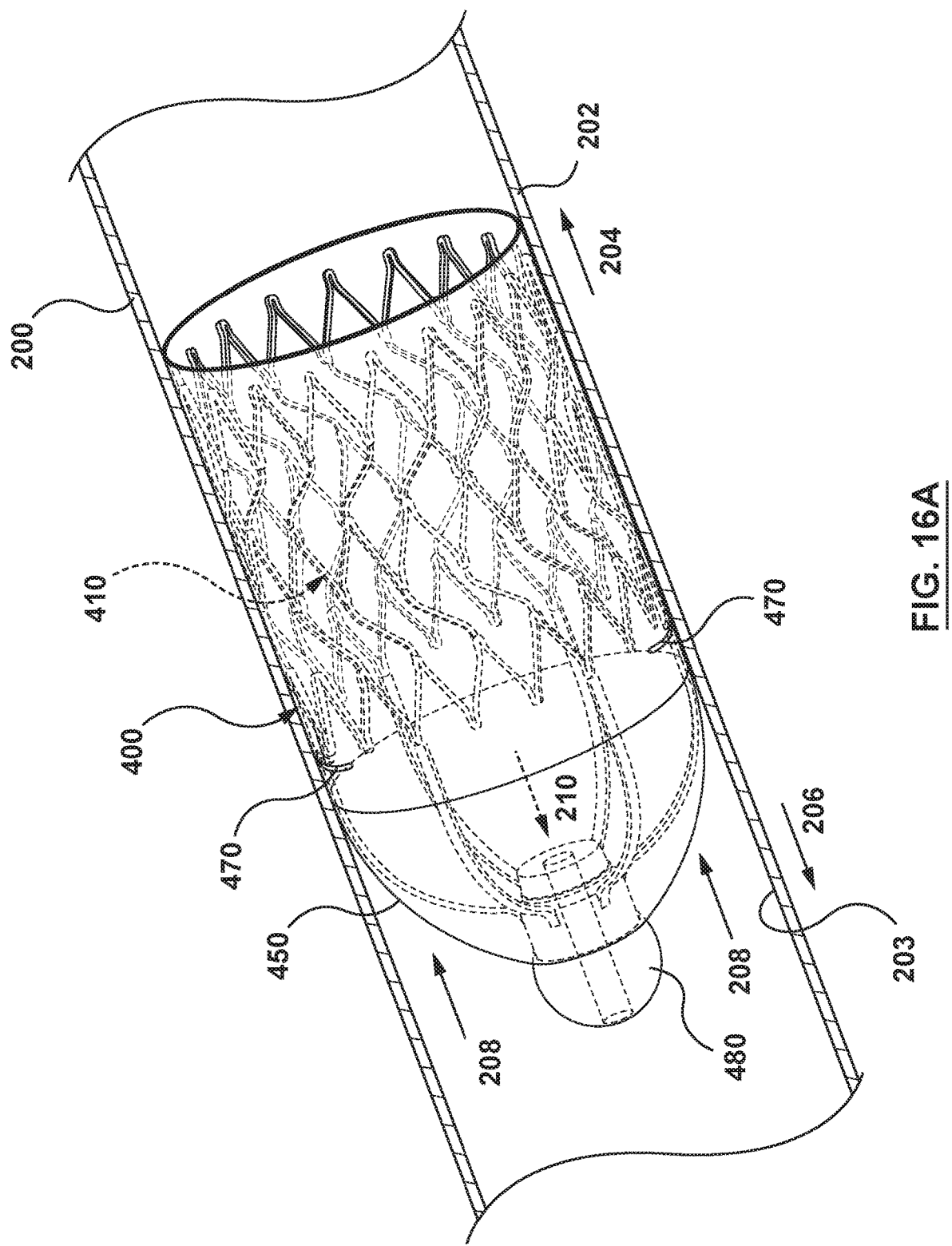
FIG. 16A is a schematic illustration of the venous valve prosthesis of FIG. 15 deployed in a vein in a closed configuration.
Figure 16B:
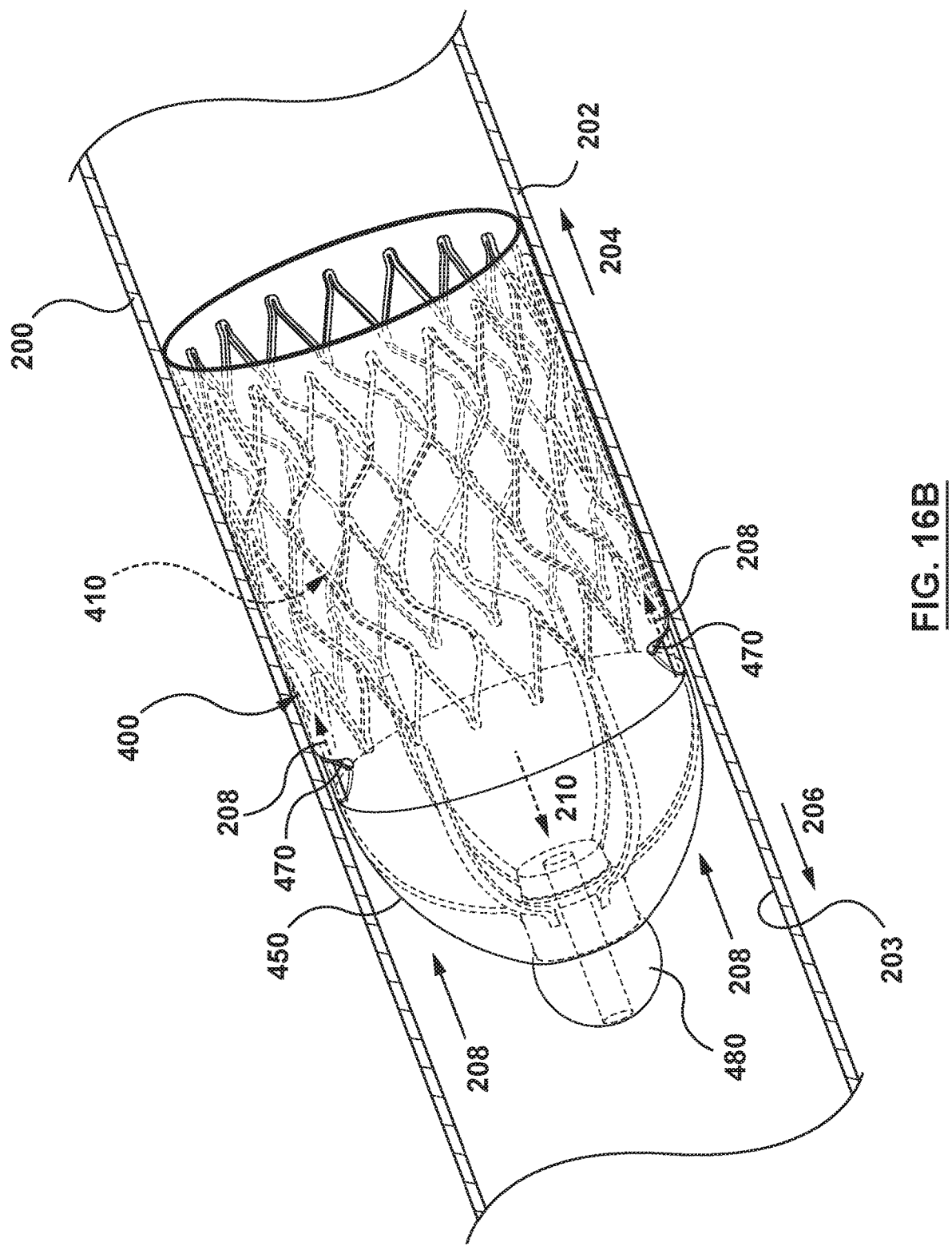
FIG. 16B is a schematic illustration of the venous valve prosthesis of FIG. 15 deployed in a vein in an open configuration.

In yet another exemplary embodiment, FIGS. 15 and 16A-16B show a venous valve prosthesis 400 according to another embodiment hereof. The venous valve prosthesis 400 includes an upstream end 404 and a downstream end 402. The venous valve prosthesis 400 includes a frame 410, a prosthetic valve 450, and a nose-piece 480 coupling the prosthetic valve 450 to the frame 410. In the embodiment of FIG. 15, the prosthetic valve 450 is coupled to an outer surface of the frame 410, but it could alternatively be coupled to an inner surface of the frame 410.

FIG. 15 shows the venous valve prosthesis 400 in a radially expanded deployed configuration. The venous valve prosthesis 400 may also be crimped into a radially compressed delivery configuration, as explained in more detail below. The frame 410 is a support structure for maintaining the venous valve prosthesis 400 in a desired location in a vein, as explained in more detail below. The frame 410 may also be referred to as a stent. As shown in FIG. 15, the frame 410 includes a valve section 414 and a stabilizing section 412 coupled to the valve section 414. Although the valve section 414 and the stabilizing section 412 are described separately, they may be formed of unitary structure or may be formed separately and attached to each other.

The valve section 414 of the frame 110 includes a hub 432 at an upstream end 418 of the valve section 414, and a plurality of struts 430 extending in a downstream direction from the hub 432. The hub 432 has a reduced diameter as compared to the deployed diameter of the stabilizing section 412. The struts 430 extend radially outward from the hub 432 in an umbrella-like fashion to a larger diameter at a downstream end 420 of the valve section 414. In the embodiment shown, there are six struts 430. However, there may be more or fewer struts 430.

The stabilizing section 412 of the frame 410 includes an upstream end 424 coupled to the downstream end 420 of the valve section 414. The stabilizing section 412 further includes a downstream end 426. The stabilizing section 412 may be a cylindrical stent as in known in the art. In the particular embodiment shown, the stabilizing section 412 includes a plurality of rings, each of the rings including a plurality of struts 438 formed in a zig-zag fashion land coupled to each other by corresponding bends 440. The rings are coupled to adjacent rings by connectors 439. The struts 438, bends 440, and connectors 439 form openings 442 therebetween, as known in the art. The stabilizing section 412 may be generally cylindrical tube as known in the art, and can be formed using various stent designs and formation methods.

Although the frame 410 has been described in parts, the frame 410 may be constructed as a single, unitary piece, or the frame 410 may be constructed as separate pieces and joined together by any suitable method, such as by welding, fusion, adhesives, or mechanical attachment. The struts 430, 438, the hub 432, the bends 440, and the connectors 439 of the frame 410 may be made of materials generally known for use in stents. For example, and not by way of limitation, the frame 410 may be made from materials commonly used for stents, such as stainless steel, Nitinol (nickel-titanium shape memory alloy), Elgiloy® (cobalt-chromium-nickel alloy), some biocompatible plastics, as well as combinations thereof. The frame 410 may be self-expanding or may be balloon expandable.

The frame 410 may include other features not shown. For example, and hot by way of limitation, the frame 410 may include barbs or hooks to assist in holding the frame 410 in the desired location in a vein.

The prosthetic valve 450 is shown in FIGS. 15 and 16A-16B coupled to the frame 410 and generally following the contours of the frame 410. The prosthetic valve 450 includes an upstream end 452 and a downstream end 454. The prosthetic valve 450 is a thin layer of material defining a conduit 460 therethrough. The upstream end 452 includes an upstream opening 456 and the downstream end 454 includes a downstream opening 458 defining upstream and downstream ends of the conduit 460. The prosthetic valve 450 includes a tapered surface 462 which generally follows the contour of the valve section 414 of the frame 410. The tapered surface 462 extends from a cylindrical surface 472 towards the upstream end 456 of the prosthetic valve 450 such that a diameter of the conduit 460 at the cylindrical surface 472 is larger than a diameter of the conduit at the upstream end 456. In a non-limiting example, the upstream opening may be in the range of 0.050-0.080 inches (1.27-2.032 mm) in diameter and the diameter of the conduit at the cylindrical surface 472 may be in the range of 0.217-0.453 inches (5.5-11.5 mm) with the venous valve prosthesis 400 in the radially expanded configuration.

The prosthetic valve 450 includes an outer surface 466 and an inner surface 468. The thickness of the prosthetic valve 450 may be in the range of 0.007-0.016 inches (0.178-0.406 mm). The prosthetic valve 450 may be made from, for example, silicone, ePTFE, or any other biocompatible flexible material.

The prosthetic valve 450 shown in FIGS. 15 and 16A-16B includes a pair of slits 470 extending through the thickness of the prosthetic valve 450 from the outer surface 466 through the inner surface 468. In the embodiment shown in FIG. 15, the slits 470 extend circumferentially around a portion of the circumference of the prosthetic valve 450 and are diametrically opposed with respect to each other. However, there may be more or fewer slits 470 and they may be arranged differently than the particular embodiment shown.

The nose-piece 480 may couple the prosthetic valve 450 to the frame 410. As shown in FIG. 15, the nose-piece 480 may include a bulbous nose 481 which abuts against the upstream end 452 of the prosthetic valve 450, and a shaft 484 which is sized to extend through the opening 456 at the upstream end 452 of the prosthetic valve 450. The shaft 484 extends through an upstream portion of the conduit 460 to a location where the shaft 484 engages the upstream hub 432 of the valve section 414 of the frame 410. The shaft 484 may engage the hub 432 by a friction fit connection, or may include perturbations which match openings in the hub 432. The nose-piece 480 includes a conduit 482 extending therethrough which is in communication with the conduit 460 of the prosthetic valve 450. The conduit 482 may be in the range of 0.016-0.050 inches (0.406-1.27 mm) in diameter.

Although the venous valve prosthesis 400 shown in FIGS. 15 and 16A-16B is shown with a nose-piece 480, the venous valve prosthesis 400 may not include a nose-piece 480. For example, and not by way of limitation, the prosthetic valve 450 may taper to the desired size for the upstream opening 456. Further, the prosthetic valve 450 may be coupled to the frame 410 by a friction fit, mechanical connection such as sutures, an adhesive connection, or other connections.

FIG. 16A shows the venous valve prosthesis 400 implanted into the vein 200 in the radially expanded configuration and in a closed configuration. In FIG. 16A the arrow 204 represents the downstream direction (towards the heart) and the arrow 206 represents the upstream direction (away from the heart).

In the radially expanded configuration, the frame 410 pushes the prosthetic valve 450 radially outward and in contact with the inner surface 203 of the wall 202 of the vein 200. Accordingly, blood flow 208 in the downstream direction 204 is blocked between the outer surface 466 of the prosthetic valve 450 and the inner surface 203 of the wall 202. This closed configuration shown in FIG. 16A occurs when the vein 200 is relaxed and not attempting to push blood in the downstream direction 204.

The conduit 482 through the nose-piece 480 in communication with the conduit 460 through prosthetic valve 450 enables a small amount of flow in the upstream direction 206, as shown by arrow 210 in FIG. 16A. As explained above, a potential deficiency with existing venous valve prostheses is the development of thrombosis on the venous valve prosthesis. It is believed that this small amount of flow assists in preventing thrombosis on the prosthetic valve 450.

When pressure is exerted to push blood in the downstream direction 208, the slits 470 of the prosthetic valve 450 open, enabling blood to flow through the slits 470 and into conduit 460, as shown in FIG. 16B. The slits 470 may open by the valve section 414 of the frame 410 compressing while the stabilizing section 412 of the frame 410 remains expanded. Thus, in the example given the stabilizing section 412 of the frame exerts a greater radial force than the valve section 414 of the frame 410.

In an alternative embodiment, the slits 470 may be located on the tapered surface 462 of the prosthetic valve 450, and the frame 410 does not compress at all. In such an embodiment, the slits may be configured to open when pressure is exerted to push blood in the downstream direction 208, but to close when no pressure is exerted in the downstream direction 208 and/or when pressure is exerted in the upstream direction 206. For example, the slits 470 may be tapered such that the slits only open when pressure is exerted to push blood in the downstream direction 208.

While various embodiments of venous valve prostheses have been described above, it should be understood that they have, been presented by way of example and illustration only, and not limitation. It will be apparent to persons skilled in the relevant art that various changes in form and detail can be made therein without departing from the spirit and scope of the invention. Further, each feature of each embodiment discussed herein, and of each reference cited herein, can be used in combination with the features of any other embodiment. For example, and not by way of limitation, the notches of the embodiment of FIGS. 9-14 may be used in the embodiment of FIGS. 1-8 or the embodiment of FIGS. 15-16. Similarly, the slits of the embodiment of FIGS. 15-16 may be used in the embodiment of FIGS. 1-8 or the embodiment of FIGS. 9-14.

Exemplary materials for the prosthetic valve 150, 350, 450 have been provided above. Further, it is desirable for the material for the prosthetic valve 150, 350, 450 to prevent or discourage thrombosis formation thereon when implanted. In an embodiment, the material used for the prosthetic valve may have inherent anti-thrombogenic/anti-biofouling properties. Such materials tend to have properties that prevent the adsorption of proteins and attachment of platelets. For example, and not by way of limitation, ePTFE may be used for the prosthetic valve.

In another embodiment, the outer surface 166, 366, 466 and/or the inner surface 168, 368, 468 of the prosthetic valve 150, 350, 450 may be treated or coated to make them more resistant to protein/platelet accumulation. In an embodiment, the treatment may make the material more inert to biological processes. In another embodiment, the treatment may be bio-active in nature and directly intervene in a biological process to prevent thrombosis.

Examples of anti-thrombogeneic coatings or treatments includes, but are not limited to, parylene, Endexo™ available from Interface Biologies, CBAS® Heparin Surface (CARMEDA® BioActive Surface), polyvinylpyrrolidone and heparin.

In another embodiment, the material for the prosthetic valve 150, 350, 450 is selected from materials that rapidly passivate. Such materials provide an environment that enables the recruitment and proliferation of endothelial cells on the surface of the material. Once passivated with endothelial cells, the material is less reactive in terms of protein absorption and less prone to thrombosis. A non-limiting, example of such an approach changes the surface chemistry of the material (for example, surface, charge, surface pH, wettability of the material) with a coating or surface modification to make it friendlier for cellular recruitment and proliferation. Non-limiting, examples of such an approach include using photoreactive azide treatment to change the hydrophobic of the material and plasma treatment to modify the surface chemistry of the material.

Other embodiments to make the material of the prosthetic valve 150, 350, 450 less susceptible to thrombosis include changing the surface topography of the material, or employing porous materials that can accommodate cell growth and proliferation. Examples of changing the surface topography include, but are not limited to, sputter coating, adding of hydroscopic hydrogels, etching, spray coating, and vapor deposition.

Figure 17:
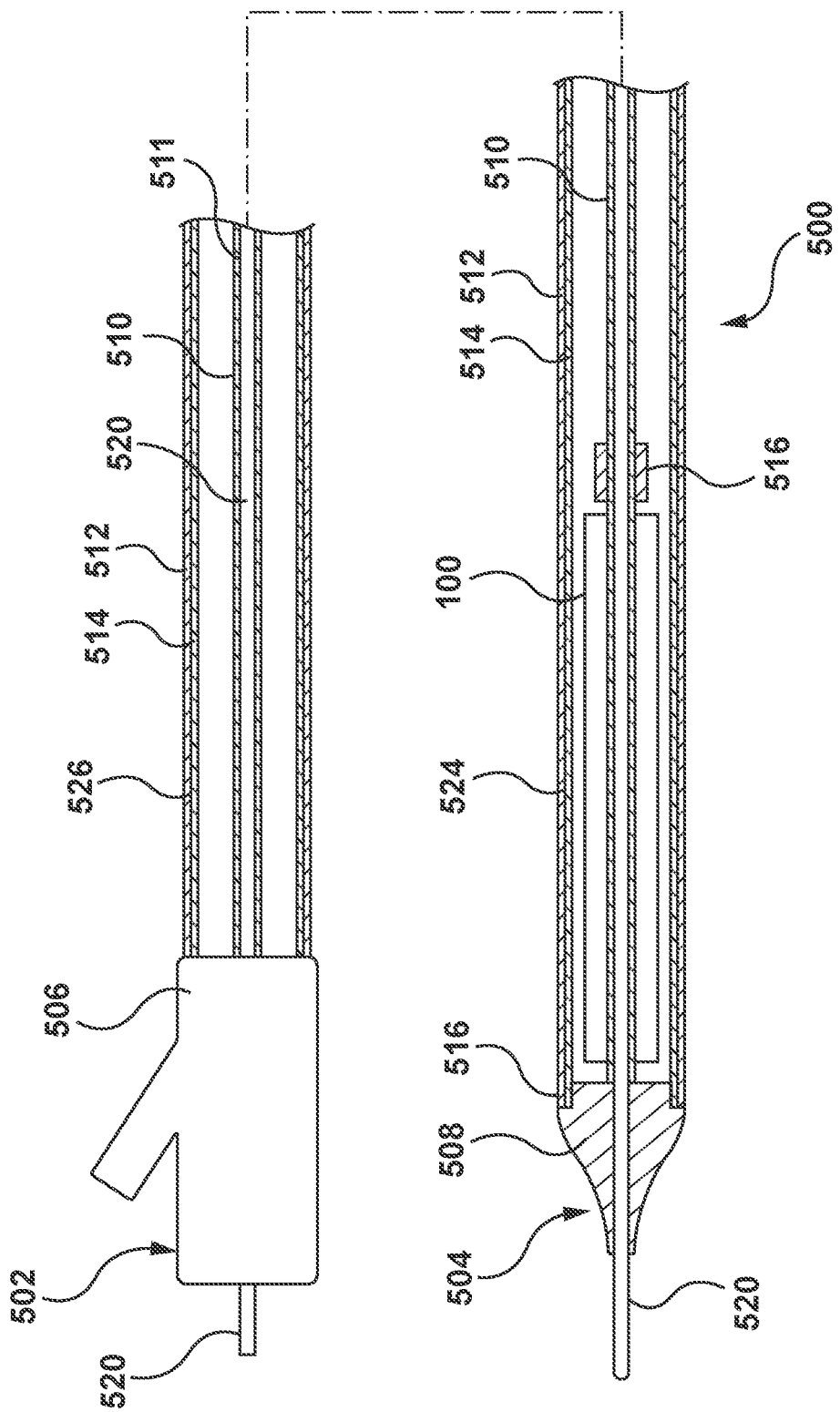
FIG. 17 is a schematic illustration of a delivery device for delivering a venous valve prosthesis.

FIGS. 17-18 show a delivery device 500 for use to deliver a venous valve prosthesis of the present invention. Although FIGS. 17-18 show the delivery device 500 with the venous valve prosthesis 100 of FIGS. 1-8 disposed therein, the delivery device 500 may be used with the venous valve prosthesis 300 of FIGS. 9-14, the venous valve prosthesis 400 of FIGS. 15-16, or any other similar embodiments that are within the scope of the claims.

The delivery device 500 includes a proximal end 502 and a distal end 504. A handle 506 is disposed at the proximal end 502. The handle 506 may be a luer type device and may include items known to those skilled in the art, such as, but not limited to, seals, actuators, gaskets, strain reliefs, etc. A tip 508 is disposed at the distal end 504 of the delivery device 500.

The delivery device 500 includes an inner shaft 510, a sheath 512 disposed around the inner shaft 510, and a runner 514 disposed between the inner shaft 510 and the sheath 512. In the embodiment shown, the inner shaft 510, the sheath 512, and the runner 514 run substantially the length of the delivery device 500 in an over-the-wire manner. However, those skilled in the art would recognize that a rapid exchange type device may also be utilized.

The inner shaft 510 is a hollow shaft which includes a guidewire lumen 511 disposed therethrough. Guidewire lumen 511 is sized and shaped to receive guidewire 520, as known in the art. The inner shaft 510 is coupled to the tip 508 at the distal end 504 and attached to the handle 506 at the proximal end 502.

The sheath 512 is a hollow, elongate tube which surrounds the inner shaft 510. A distal end 516 of the sheath 512 interacts with the tip 508. The distal end 516 of the sheath 512 may abut a proximal end of the tip 508 or may overlap a proximal portion of the tip 508, as shown in FIG. 17. The sheath 512 is coupled to the handle 506 such that the sheath 512 may be moved longitudinally relative to the inner shaft 510. The sheath 512 is sized and shaped to confine the venous valve prosthesis 100 in the radially compressed delivery configuration.

The runner 514 is disposed between the inner shaft 510 and the sheath 512. A distal portion 518 of the runner 514 includes a plurality of runners 522 with slots 524 disposed therebetween, as best seen in FIG. 18 and described in more detail below. A proximal portion 526 of the runner 514 is a hollow shaft. The runners 522 are disposed between the venous valve prosthesis 100 and the sheath 512 with the venous valve prosthesis 100 in the radially compressed delivery configuration and the delivery device 500 in the delivery configuration, as shown in FIG. 17. The runners 522 protect the venous valve prosthesis 100 during loading into the sheath 512.

The delivery device 500 may further include a pusher 516 that abuts against an end of the venous valve prosthesis 100 such that the venous valve prosthesis 100 does not move while the sheath 512 is being retracted. The pusher 516 is shown in FIG. 17 attached to the inner shaft 510, but the pusher 516 may be any similar device to maintain the venous valve prosthesis 100 in place while retracting sheath 512. Further, the pusher 516 may include an attachment mechanism which couples the pusher to a portion of the venous valve prosthesis 100. The attachment mechanism may be configured to release the venous valve prosthesis after the sheath 512 has been retracted. Spindles with protrusions about which a portion of the venous valve prosthesis is held are non-limiting examples of such attachment mechanisms. Such attachment mechanisms may also be referred to as capture mechanisms.

The delivery device 500 is advanced through the vasculature to a location such that the venous valve prosthesis 100 disposed therein is located at a desired site for implantation of the venous valve prosthesis 100. Access to the vasculature is achieved by known methods. The implantation site is a vein, including veins in both the superficial and deep venous systems, such as, but not limited to, greater saphenous veins, lesser saphenous veins, anterior and posterior tibial veins, popliteal veins; and femoral veins. The implantation site is preferably spaced from a native venous valve.

With the delivery device 500 advanced such that the venous valve prosthesis 100 is at the desired implantation site, the sheath 512 is retracted. The sheath 512 may be retracted using actuators located on handle 506 or other retraction methods. FIG. 18 shows the delivery device 500 with the sheath 512 retracted. As can be seen in FIG. 18, the venous valve prosthesis 100 is self-expanding such that release from the sheath 512 enables the venous valve prosthesis 100 to radially expand. However, as also seen in FIG. 18, the plurality runners 522 of the runner 514 remain disposed around the venous valve prosthesis 100. The runners 522 do not resist the radial expansion of the venous valve prosthesis 100 in the manner that the sheath 512 resists expansion. Therefore, the venous valve prosthesis 100 radially expands itself and the runners 522 when released from the sheath 512. However, the plurality of runners 522 do enable the sheath 512 to be advanced back over the venous valve prosthesis 100 to radially compress the venous valve prosthesis 100 for various reasons, such as relocation of the venous valve prosthesis 100 or abortion of the procedure. A transition area 528 of the runner 514, shown in FIG. 18, provides a smooth inclined surface for the sheath 512 to be advanced back over the venous valve prosthesis 100.

If the physician is satisfied with the placement of the venous valve prosthesis 100, the runner 514 is retracted, leaving the venous valve prosthesis 100 implanted in the vein, as shown in FIG. 5. The runner 514 may be retracted using actuators located on handle 506 or other retraction methods.

With the venous valve prosthesis 100 implanted as shown in FIG. 5, the delivery device 500 may be removed from the patient.

Alternatively, the venous valve prosthesis 100 may be implanted through a surgical procedure. For example, the vein may be exposed using a cut down procedure, which may enable a surgeon to better assess the proper size of the venous valve prosthesis 100 to be inserted into the vein, as well as assess the proper placement of the venous valve prosthesis 100.

Further, as described above with respect to the embodiment shown in FIGS. 1-8, the venous valve prosthesis 100 may include a valve section 114 and a stabilizing section 112 that are configured to be different sizes. For example, one section may be configured to be 10% larger in diameter than the other section. In such an embodiment, both sections 112, 114 may include a prosthetic valve 150. The surgeon may then assess the vein to determine the proper size valve, and remove the prosthetic valve 150 from the section 112 or 114 that is not the proper size, and that section becomes the stabilizing section 112. It is believed that a proper size for the valve section 114 and prosthetic valve 150 is one in which the prosthetic valve 150 makes contact with the inner surface 203 of the vein wall 202 without overly distending the vein wall 202.

While various embodiments according to the present invention have been described above, if should be understood that they have been presented by way of illustration and example only, and not limitation. It will be apparent to persons skilled in the relevant art that various changes in form and detail can be made therein without departing from the spirit and scope of the invention. Further, each feature of each embodiment discussed herein, and of each reference cited herein, can be used in combination with the features of any other embodiment. Thus, the breadth and scope of the present invention should not be limited by any of the above-described exemplary embodiments, but should be defined only in accordance with the appended claims and their equivalents.

What is claimed is:

1. A venous valve prosthesis comprising:
a frame comprising a valve section and a stabilizing section, wherein the stabilizing section is configured to anchor the venous valve prosthesis within a vessel of a patient, the valve section being configured to compress radially inward from a radially expanded configuration to a radially compressed configuration, wherein the stabilizing section is configured to remain expanded when the valve section is in the radially expanded configuration and when the valve section is in the radially compressed configuration; and
a prosthetic valve coupled to the frame, wherein when the valve section is in the radially expanded configuration, the valve section applies a radially outward force on the prosthetic valve, and wherein radial compression of the valve section from the radially expanded configuration to the radially compressed configuration is configured to move the prosthetic valve from a closed valve configuration to an open valve configuration,
wherein when the venous valve prosthesis is implanted in a vessel and the prosthetic valve is in the open valve configuration, the venous valve prosthesis is configured to enable antegrade blood flow between an outer surface of the prosthetic valve and a wall of the vessel, and when the prosthetic valve in the closed valve configuration, an outer surface of the prosthetic valve is in contact with the wall of the vessel around a perimeter of the prosthetic valve to prevent blood from flowing past the prosthetic valve between the wall of the vessel and the outer surface of the prosthetic valve.

2. The venous valve prosthesis of claim 1, wherein the stabilizing section is configured to cause at least a portion of the outer surface of the prosthetic valve to contact the wall in both the open valve configuration and the closed valve configuration.

3. The venous valve prosthesis of claim 1, wherein the prosthetic valve defines slits, and wherein in the open valve configuration, the slits are opened by the compression of the valve section to enable antegrade blood flow upstream of the slits and through the slits.

4. The venous valve prosthesis of claim 1, wherein the frame comprises a plurality of struts and openings defined between the plurality of struts.

5. The venous valve prosthesis of claim 1, wherein the prosthetic valve is coupled to the valve section of the frame.

6. The venous valve prosthesis of claim 1, wherein the frame is a self-expanding frame.

7. The venous valve prosthesis of claim 6, wherein the stabilizing section of the frame is configured to exert a first radially outward force that is greater than a second radially outward force exerted by the valve section of the frame.

8. The venous valve prosthesis of claim 1, wherein the prosthetic valve includes a tapered surface and a non-tapered surface.

9. The venous valve prosthesis of claim 8, wherein the non-tapered surface includes a substantially cylindrical surface adjacent a larger end of the tapered surface.

10. The venous valve prosthesis of claim 9, wherein the substantially cylindrical surface defines slits, wherein in the open valve configuration, the slits are opened by the compression of the valve section to enable antegrade blood flow upstream of the slits and through the slits.

11. The venous valve prosthesis of claim 1, wherein the valve section is configured to compress radially inward from the radially expanded configuration to the radially compressed configuration in response to a pressure exerted within the vessel to push blood in a downstream direction, and wherein the stabilizing section is configured to not radially compress in response to the pressure.

12. The venous valve prosthesis of claim 1, wherein the prosthetic valve defines an opening through a middle portion of the prosthetic valve, wherein the opening is open in both the open valve configuration and the closed valve configuration.

13. The venous valve prosthesis of claim 1, wherein the valve section includes a hub at an upstream end of the valve section and a plurality of struts extending in a downstream direction from the hub and radially outward from the hub.

14. The venous valve prosthesis of claim 1, wherein the valve section and the stabilizing section are part of a single, unitary frame.

15. The venous valve prosthesis of claim 1, wherein the valve section and the stabilizing section are separate pieces that are joined together.

16. The venous valve prosthesis of claim 1, wherein the prosthetic valve is disposed about an exterior of the frame.

17. The venous valve prosthesis of claim 1, wherein the prosthetic valve is disposed within an interior of the frame.

18. The venous valve prosthesis of claim 1, wherein the frame is a balloon-expandable frame.

19. A venous valve prosthesis comprising:
a frame comprising a valve section and a stabilizing section, wherein the stabilizing section is configured to anchor the venous valve prosthesis within a vessel of a patient, and wherein when the venous valve prosthesis is implanted in a vessel, the valve section is configured to compress radially inward from a radially expanded configuration to a radially compressed configuration in response to a pressure exerted within the vessel to push blood through the vessel, the stabilizing section being configured to not radially compress in response to the pressure; and
a prosthetic valve coupled to the frame such that radial compression of the valve section from the radially expanded configuration to the radially compressed configuration moves the prosthetic valve from a closed valve configuration to an open valve configuration, wherein when the valve section is in the radially expanded configuration, the valve section applies a radially outward force on the prosthetic valve,
wherein when the venous valve prosthesis is implanted in the vessel and the prosthetic valve is in the open valve configuration, the venous valve prosthesis is configured to enable antegrade blood flow between an outer surface of the prosthetic valve and a wall of the vessel, and when the prosthetic valve in the closed valve configuration, an outer surface of the prosthetic valve is in contact with the wall of the vessel around a perimeter of the prosthetic valve to prevent blood from flowing past the prosthetic valve between the wall of the vessel and the outer surface of the prosthetic valve.

20. The venous valve prosthesis of claim 19, wherein the prosthetic valve defines an opening through a middle portion of the prosthetic valve, wherein the opening is open in both the open valve configuration and the closed valve configuration.

21. A method comprising:

delivering a venous valve prosthesis to a site in a vessel of a patient, wherein the venous valve prosthesis includes a frame and a prosthetic valve coupled to the frame, the frame comprising a valve section and a stabilizing section; and deploying the venous valve prosthesis at the site in the vessel, wherein the stabilizing section is configured to anchor the venous valve prosthesis within the vessel, the valve section being configured to compress radially inward from a radially expanded configuration to a radially compressed configuration, wherein the stabilizing section is configured to remain expanded when the valve section is in the radially expanded configuration and when the valve section is in the radially compressed configuration;

wherein when the valve section is in the radially expanded configuration, the valve section applies a radially outward force on the prosthetic valve, and wherein when the venous valve prosthesis is implanted in a vessel and the prosthetic valve is in the open valve configuration, the venous valve prosthesis is configured to enable antegrade blood flow between an outer surface of the prosthetic valve and a wall of the vessel, and when the prosthetic valve in the closed valve configuration, an outer surface of the prosthetic valve is in contact with the wall of the vessel around a perimeter of the prosthetic valve to prevent blood from flowing past the prosthetic valve between the wall of the vessel and the outer surface of the prosthetic valve.

22. The method of claim 21, wherein delivering the venous valve prosthesis to the site in the vessel comprises transluminally delivering the venous valve prosthesis to the site.

23. The method of claim 21, wherein delivering the venous valve prosthesis to the site comprises delivering the venous valve prosthesis in a radially compressed delivery configuration to the site, and wherein deploying the venous valve prosthesis comprises expanding the venous valve prosthesis to a radially expanded deployed configuration.

24. The method of claim 23, wherein the frame is self-expanding and expanding the venous valve prosthesis comprises releasing the frame from a sheath.

25. The method of claim 23, wherein the frame is balloon-expandable and expanding the venous valve prosthesis comprises inflating a balloon disposed within the frame to expand the frame.

* * * * *